(12) United States Patent
Silverman et al.

(10) Patent No.: US 7,470,790 B2
(45) Date of Patent: Dec. 30, 2008

(54) HETEROAROMATIC SELECTIVE INHIBITORS OF NEURONAL NITRIC OXIDE SYNTHASE

(75) Inventors: Richard B. Silverman, Northbrook, IL (US); Haitao Ji, Evanston, IL (US)

(73) Assignee: Northwestern University, Evanston, IL (US)

( * ) Notice: Subject to any disclaimer, the term of this patent is extended or adjusted under 35 U.S.C. 154(b) by 376 days.

(21) Appl. No.: 10/935,911

(22) Filed: Sep. 8, 2004

(65) Prior Publication Data

US 2005/0107369 A1 May 19, 2005

Related U.S. Application Data

(60) Provisional application No. 60/500,997, filed on Sep. 8, 2003.

(51) Int. Cl.
*C07D 401/04* (2006.01)
*C07D 401/14* (2006.01)

(52) U.S. Cl. ............. 546/278.4; 546/278.7; 546/279.1; 546/256

(58) Field of Classification Search .............. 546/278.4, 546/279.1, 256, 278.7
See application file for complete search history.

(56) References Cited

U.S. PATENT DOCUMENTS

| | | | |
|---|---|---|---|
| 6,500,853 B1 | 12/2002 | Seehra et al. | |
| 6,525,182 B1 | 2/2003 | Goodman et al. | |
| 7,056,945 B1 | 6/2006 | Poulos et al. | |
| 2003/0119751 A1 | 6/2003 | Silverman et al. | |
| 2005/0107369 A1 | 5/2005 | Silverman et al. | |

*Primary Examiner*—Patricia L Morris
(74) *Attorney, Agent, or Firm*—Reinhart Boerner Van Deuren s.c.

(57) ABSTRACT

Compounds inhibiting neuronal nitric oxide synthase (nNOS) for potential treatment in neurodegenerative diseases, such as stroke, Alzheimer's disease, Parkinson's disease, Huntington's disease, such compounds of a formula.

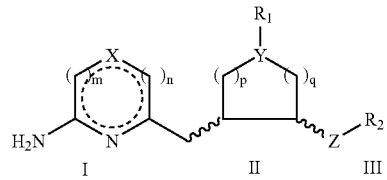

10 Claims, 5 Drawing Sheets

*Trans* isomers:

*Cis* isomers:

*Trans* isomers

*Cis* isomers

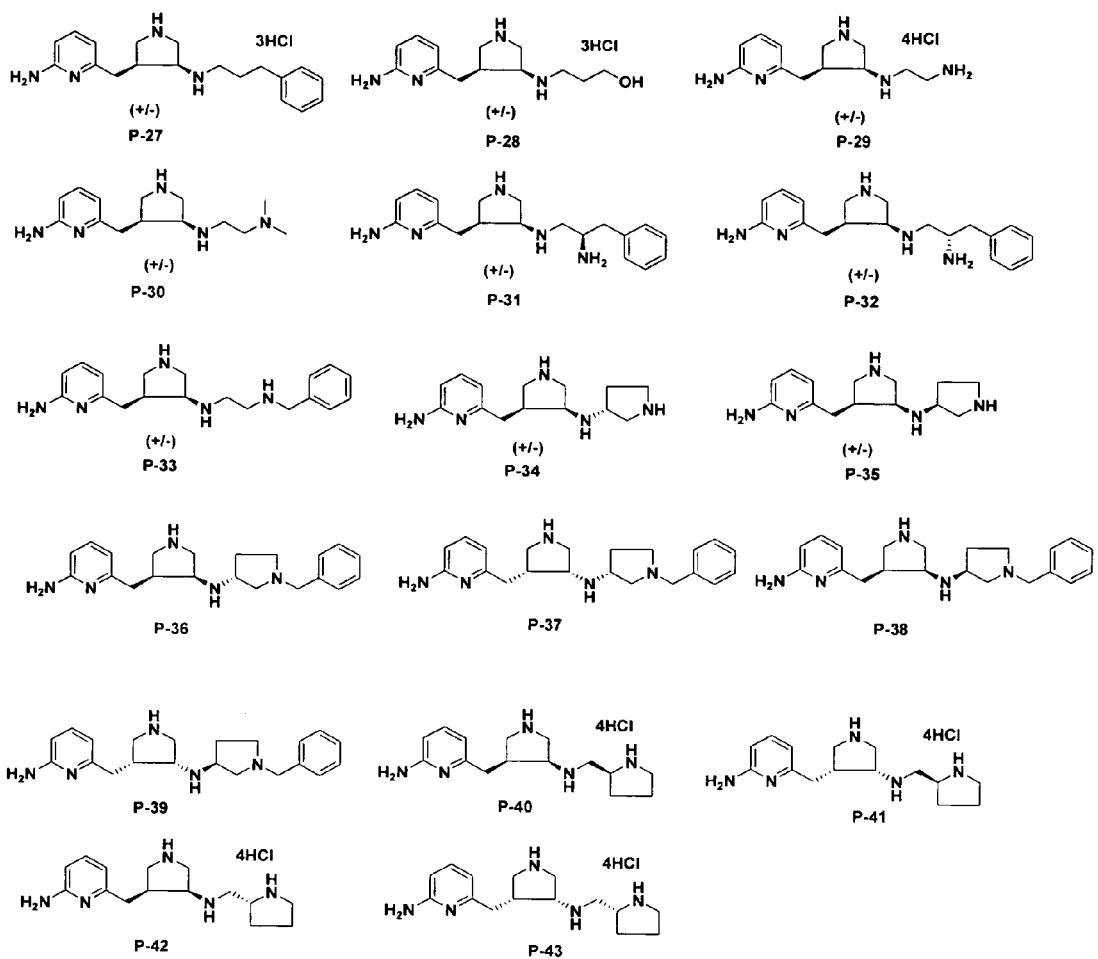
Fig. 3, con't

P-44

P-45

P-46

P-47

HETEROAROMATIC SELECTIVE INHIBITORS OF NEURONAL NITRIC OXIDE SYNTHASE

This application claims priority benefit from application Ser. No. 60/500,997 filed Sep. 8, 2003, the entirety of which is incorporated herein by reference.

The United States Government has certain rights to this invention pursuant to grant No. GM49725 from the National Institutes of Health to Northwestern University.

BACKGROUND OF INVENTION

Nitric oxide (NO) is synthesized enzymatically from arginine in numerous tissues and cell types by a family of enzymes, collectively known as nitric oxide synthase (NOS, E.C. 1.14.13.39). Three principal isoforms of this enzyme have been isolated and characterized, each associated with different physiological functions: the immune response (inducible NOS or iNOS), smooth muscle relaxation (endothelial NOS or eNOS), and neuronal signaling (neuronal NOS or nNOS). All of these isoforms utilize NADPH, FAD, FMN, (6R)-5,6,7,8-tetrahydrobiopterin and heme as cofactors.

Overproduction of NO has been a factor in numerous disease states. NO overproduction by nNOS has been implicated in strokes, migraine headaches, Parkinson's disease, Alzheimer's disease, and with tolerance to and dependence on morphine. iNOS-mediated overproduction of NO has been associated with development of colitis, tissue damage and inflammation, and rheumatoid arthritis.

Animal studies and early clinical trials suggest that NOS inhibitors could be therapeutic in many of these disorders; however, because of the importance of nitric oxide to physiological functioning, potent as well as isoform-selective inhibitors are essential. nNOS inhibition has been targeted for treatment of strokes and Parkinson's disease, and iNOS inhibition for the treatment of septic shock and arthritis. Although there may be pathologies associated with overactivity of eNOS, blood pressure homeostasis is so critical that most investigators believe that therapeutically useful NOS inhibitors should not inhibit eNOS.

Excellent inhibitory potency and selectivity for nNOS over eNOS and iNOS have been achieved with certain prior art nitroarginine dipeptide amides that have an amine-containing side chain (cpds. 1-3 in the cited reference). See Huang, H.; Martasek, P.; Roman, L. J.; Masters, B. S. S.; Silverman, R. B. N$^{\omega}$-Nitroarginine-Containing Dipeptide Amides. Potent and Highly Selective Inhibitors of Neuronal Nitric Oxide Synthase. *J. Med Chem.* 1999, 42, 3147-53.

The most potent nNOS inhibitor among these compounds is L-Arg$^{NO2}$-L-Dbu-NH$_2$ (1) ($K_i$=130 nM), which also shows excellent selectivity over eNOS (>1500-fold) and 192-fold selectivity over iNOS. Further peptidomimetic modifications are, however, invariably necessary before such compounds can be therapeutically useful. Generally, peptides have poor bioavailability and, for that reason, are often unsuccessful as drug candidates.

SUMMARY OF INVENTION

Figure 1:
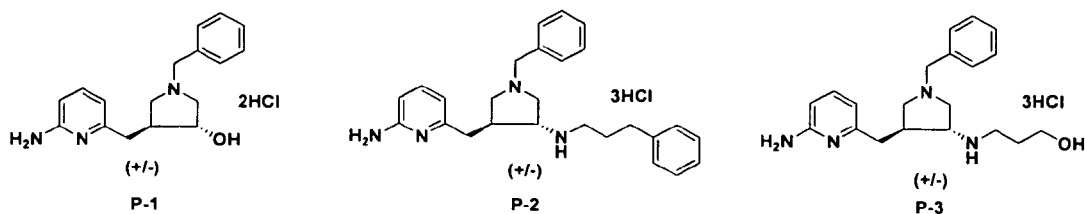
FIGS. 1-3 provide cis and trans isomers of compounds in accordance with this invention.
Figure 1:
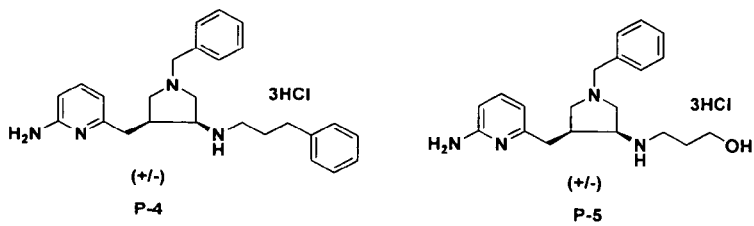

In light of the foregoing, it is an object of the present invention to provide compounds and related methods of use for the selective inhibition of neuronal nitric oxide synthase, thereby overcoming various deficiencies and shortcomings of the prior art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It is an object of the present invention to provide one or more non-peptide compounds exhibiting selective nNOS, inhibition, over other enzyme isoforms.

It is an object of the present invention to provide one or more conformationally-constrained compounds for selective NOS inhibition.

It can also be an object of this invention to provide such non-peptide, conformationally-constrained compounds for in vitro use and study under conditions promoting nitric oxide production, indicative of one or more mammalian disease states.

Alternatively, it is an object of the present invention to provide a molecular structure or such compounds enabling in vivo treatment of such disease states.

Other objectives, features, benefits and advantages of the present invention will be apparent from this summary and its descriptions of certain embodiments of such compounds, and will be readily apparent to those skilled in the art having knowledge of the synthetic techniques described therewith. Such objectives, features, benefits and advantages will be apparent from the above as taken into conjunction with the accompanying examples, data, figures and all reasonable inferences to be drawn therefrom.

Crystal structures of the oxygenase domain of the three NOS iosforms were previously determined. A new de novo molecular design method was then developed to design the nNOS inhibitors of this invention. Residues in the active site of nNOS considered important for ligand binding were analyzed by the Multiple Copy Simultaneous Search (MCSS) method. The structural differences in the active site among the three NOS isoforms were also analyzed by the GRID/CPCA method. Then, the molecules were constructed by the LUDI library design and LUDI fragment connection. The suitable LUDI fragment library was constructed according to the results of GRID and MCSS analysis. The designed molecules were then docked into the active site using the commercially-available AutoDock 3.5 program. The binding scores were evaluated by the Cscore program. Finally, a property-based drug design strategy was used to evaluate the ADME effect of the molecules. If the binding score and/or property score of the molecules did not meet the requirements, the molecule was re-constructed, re-docked and re-scored, until the new molecules gave satisfactory results.

Considerations in the design of the present selective nNOS inhibitors include, whether: (1) the molecules interact with the key residues that have been identified in nNOS; (2) the molecules interact with residues that give selectivity for both nNOS/eNOS and for nNOS/iNOS; (3) the molecules are conformationally-constrained, especially, in a constrained conformation that matches the nNOS-isoform selectivity; (4) the molecules are orally absorbed and pass through the blood-brain barrier. Such an approach provided two advantages: (a) A strategy for the production of new molecules and lead compounds; (b) Results of active site analysis can be easily merged into a process for new molecular design.

Accordingly, the present invention relates, in part, to compounds of a formula.

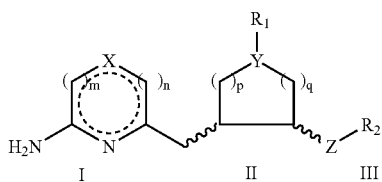

Such a compound can be considered as in the context of substructures I, II and III, as shown. Substructure I comprises an amino-substituted nitrogen-containing aromatic ring, where X can be CH, N, O, or S; and m and n can be 0 or 1, provided at least one of m and n is 1. Substructure II comprises a five- or six-membered ring, where Y can be N or CH; and p and q can be 1 or 2, provided at least one of p and q is 1 and both p and q are not concurrently 2. Further, $R_1$ can be H, alkyl, amino, hydroxy, or a substituted alkyl (e.g., but not limited to aminoalkyl or hydroxyalkyl) moiety. Substructure III can be an alkyl, substituted alkyl, alkylhydroxy (Z=O), substituted alkylhydroxy (Z=O), alkylamine (Z=NH) or a substituted alkylamine (Z=NH) moiety (e.g., but not limited to linear, cyclic alkylamine).

The structure of such a compound is limited only by choice of starting material or reagent and enroute to substructures I, II and/or III. Likewise, the present compounds are without stereochemical limitation. As illustrated below, such compounds and/or their intermediates are available as racemic mixtures from which isomers can be resolved or are diastereomers, from which cis and/or trans isomers can be separated. Further, it will be understood by those skilled in the art that the compounds of this invention can comprise an acid salt of any such compound. Without limitation, certain embodiments can be partially or fully protonated, comprising a primary, secondary and/or tertiary amine, whereby the counter ion(s) is a conjugate base of a protic acid.

Without regard to compound charge or stereochemistry, in certain embodiments, m and n are 1 and X is CH, such that substructure I can comprise an amino-substituted pyridinyl moiety. Regardless, in certain embodiments, Y is N, p is 1 or 2, and Z is NH, such that substructure II comprises, respectively, an amino-substituted pyrrolidinyl or piperazinyl moiety. Alternatively, Y can be CH and substructure II can comprise a cyclopentyl or cychohexyl moiety, where p and q can be 1 or 2, provided at least one of p and q is 1. Regardless, $R_1$ can be as described above or as illustrated elsewhere herein. $R_2$, in certain embodiments, can comprise an aminoalkyl moiety pendant to the aforementioned amino (Z is NH) substituent. Accordingly, $R_2$ can comprise any primary, secondary, or tertiary, linear or cyclic aminoalkyl group.

Alternatively, this invention can be directed to compounds of a formula.

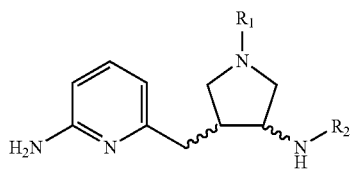

Without limitation, certain embodiments are as provided above in conjunction with the foregoing discussion regarding $R_1$ and $R_2$. Likewise, such compounds are not restricted by charge or stereochemistry.

In part, the present invention can also provide a method of inhibiting neuronal nitric oxide synthase, such a method comprises contacting a neuronal nitric oxide synthase with an effective amount of any of the present compounds, including but not limited to those illustrated by the following examples, referenced figures and/or accompanying synthetic schemes. More specifically, as also supported herein, the present invention can provide a method for selective inhibition of neuronal nitric oxide synthase. Such a method can comprise: (1) providing a compound of this invention; and (2) contacting a nitric oxide synthase with such a compound, such contact selectively inhibiting neuronal nitric oxide synthase over inducible and endothelial isoforms.

Selective inhibition of nNOS was demonstrated for representative compounds of this invention, using procedures and protocols well-known to those skilled in the art. All of the NOS isoforms used were recombinant enzymes overexpressed in *E. Coli* from different sources. Nitric oxide formation from NOS was monitored by the hemoglobin capture assay as described in the literature. The apparent $IC_{50}$ values demonstrating such inhibition were obtained by measuring percent inhibition in the presence of 10 μM L-arginine with at least three concentrations of inhibitor. Accordingly, compounds of this invention can be used in vitro for nNOS inhibition and/or in the treatment or evaluation for treatment of various neurodegeneration, including that from stroke, Alzheimer's disease, Parkinson's disease, and Huntington's disease.

EXAMPLES OF THE INVENTION

The following non-limiting examples and data illustrate various aspects and features relating to the compounds and/or methods of the present invention, including the preparation and use of various nitric oxide synthase inhibitor compounds, as are available through the synthetic methodologies described herein. In comparison with the prior art, the present compounds and related methods provide results and data which are surprising, unexpected and contrary thereto. While the utility of this invention is illustrated through the preparation and use of several compounds, it will be understood by those skilled in the art that comparable results are obtainable with various other compounds, as are commensurate with the scope of this invention.

Examples 1-8 can be considered in conjunction with Scheme I, below.

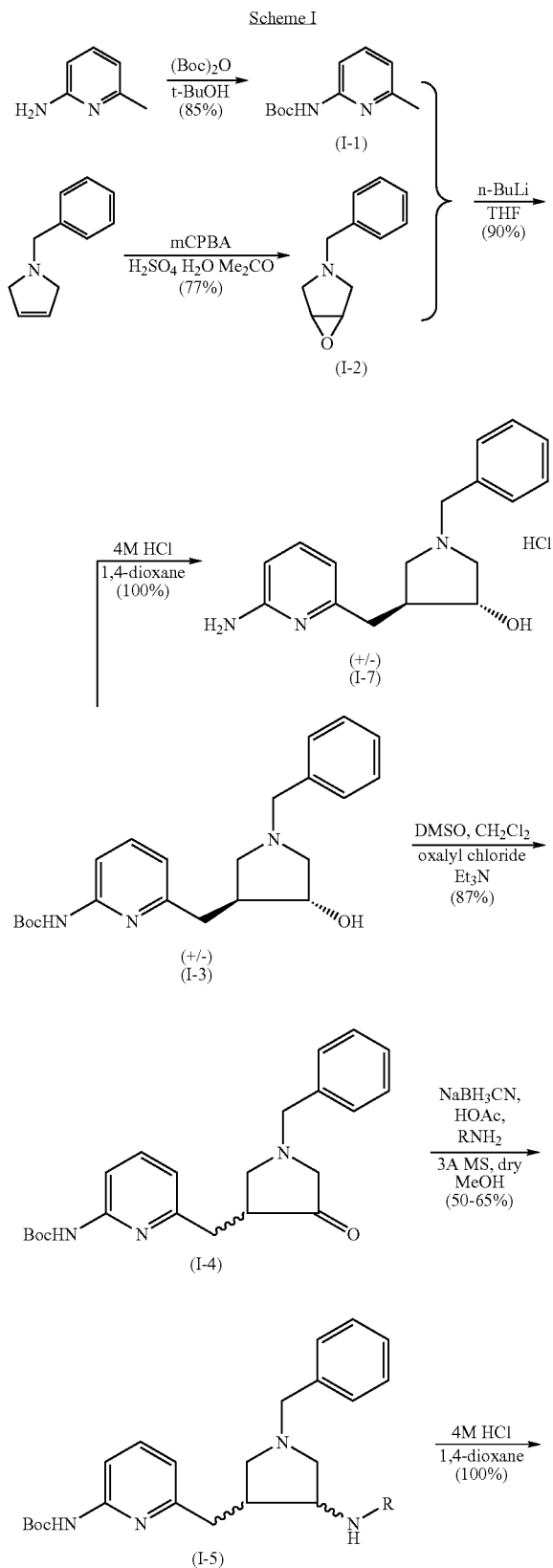

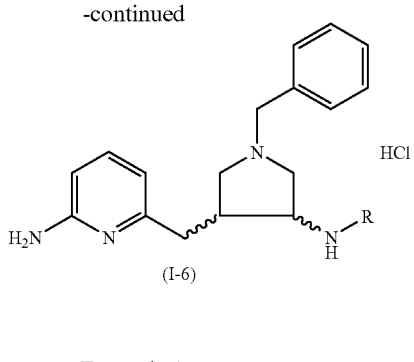

Example 1

Synthesis of (6-methyl-pyridin-2-yl)-carbamic acid tert-butyl ester (I-1)

A solution of 2-amino-6-picoline (0.025 mol) in 50 mL of melted t-butanol was treated with di-tert-butyl dicarbonate (0.0275 mol). The temperature was kept about 60° C. After the solution was stirred for 48 h, the solvent was evaporated. The residue was purified by column chromatography (silica gel, 8:2 hexanes to ethyl acetate) to obtain pure (I) in 85% yield.

Example 2

Synthesis of 3-benzyl-6-oxa-3-aza-bicyclo[3.1.0]hexane (I-2)

To an ice-cooled solution of 1-benzyl pyrroline (0.01 mol), 98% $H_2SO_4$ (0.012 mol), water (1.5 g), and acetone (10 mL) in a round bottom flask was added 77% m-CPBA (0.013 mol) with stirring, and allowed to react for about 50 h at room temperature. After completion of the reaction (TLC monitor), acetone was evaporated under reduced pressure, and the mixture was neutralized by 1M NaOH, and extracted with toluene (30 mL×3). The precipitates that appeared were filtered, and the filtrate was repeatedly washed with water (30 mL×2). After the solvent was evaporated under reduced pressure, pure product was obtained in 77% yield via column chromatography (silica gel, $CH_2Cl_2$:EtOAc:MeOH, 7.5:2.00:0.5).

Example 3

Synthesis of [6-(1-benzyl-4-hydroxy-pyrrolidin-3-ylmethyl)-pyridin-2-yl]-carbamic acid tert-butyl ester (I-3)

A solution of (6-methyl-pyridin-2-yl)-carbamic acid tert-butyl ester I-1 (0.00625 mol) in 10 mL THF was cooled in a −78° C. bath (acetone/dry ice). n-BuLi (1.6 M in hexanes, 0.0125 mol) was added during 15 min. under $N_2$. The color of solution was changed from colorless to orange. Then the cooling bath was removed. After 45 min stirring at room temperature, the color solution was changed into dark red. The solution was then returned to the −78° C. bath. 3-Benzyl-6-oxa-3-aza-bicyclo[3.1.0]hexane I-2 (0.005 mol) in 10 mL THF was added during 1 h. After 2 h, the cooling bath was removed. The solution was stirred for 2 h more at room temperature. The reaction was quenched by the addition of ice-cold water (50 ml). The mixture was extracted with $CH_2Cl_2$ (30 ml×3). The combined organic layers were washed with brine and dried over anhydrous $MgSO_4$. The solvent was removed in vacuo and the residue was purified by column chromatography (silica gel, CH$_2$Cl$_2$ MeOH, 9:1) (90%).

Example 4

Synthesis of [6-(1-benzyl-4-oxo-pyrrolidin-3-ylmethyl)-pyridin-2-yl]-carbamic acid tert-butyl ester (I-4)

To a solution of DMSO (0.02 mol) in 30 mL of anhydrous CH$_2$Cl$_2$ was added dropwise oxalyl chloride (0.015 mol). The mixture was stirred at −78° C. for 10 min. After this time a solution of [6-(1-benzyl-4-hydroxy-pyrrolidin-3-ylmethyl)-pyridin-2-yl]-carbamic acid tert-butyl ester I-3 (0.01 mol) in 10 mL of anhydrous CH$_2$Cl$_2$ was added dropwise at a rate to keep the reaction temperature below −60° C. Upon complete addition, the mixture was allowed to stir at −78° C. for 2 h. Then anhydrous triethylamine (0.03 mol) was added dropwise to the mixture. After complete addition, the reaction mixture was allowed to warm to room temperature. The resulting solution was partitioned between 1 M NaOH (40 ml) and the product was extracted with CH$_2$Cl$_2$ (30 ml×2). All organic layers were combined, washed with brine, dried over anhydrous Na$_2$SO$_4$, and concentrated in vacuo to yield crude product, which was purified using column chromatography (silica gel, CH$_2$Cl$_2$:EtOAc, 4:1) (87%).

Example 5

Synthesis of [6-(4-substituted amino-1-benzyl-pyrrolidin-3-ylmethyl)-pyridin-2-yl]-carbamic acid tert-butyl ester (I-5)

To a solution of [6-(1-benzyl-4-oxo-pyrrolidin-3-ylmethyl)-pyridin-2-yl]-carbamic acid tert-butyl ester I-4 (0.001 mol), substituted amine, such as 3-phenyl-propylamine, (0.015 mol), acetic acid (0.0015 mol), and 3 Å molecular sieves (1 g) in dry MeOH (20 mL) was added NaBH$_3$CN (0.002 mol). Then the reaction was stirred at room temperature under N$_2$ atmosphere for 36 h. TLC monitors the completion of the reaction. The reaction mixture was then filtered, and the filtrate was concentrated in vacuo. The residue was diluted with 1M NaOH (50 mL) and extracted with CH$_2$Cl$_2$ (50 ml×2). The organic layers were combined, washed with brine, dried over anhydrous MgSO$_4$. and concentrated in vacuo of solvent to give crude product, which was purified by column chromatography (silica gel, hexanes:EtOAc:Et$_3$N, 3:2:0.25 for {6-[1-benzyl-4-(3-phenyl-propylamino)-pyrrolidin-3-ylmethyl]-pyridin-2-yl}-carbamic acid tert-butyl ester) (65%). The cis and trans isomers can be separated with the above eluent. The ratio of cis and trans isomers was 45:55.

Example 6

Synthesis of 6-[1-benzyl-4-(substituted amino)-pyrrolidin-3-ylmethyl]-pyridin-2-ylamine hydrochloride salt (I-6) or 4-(6-amino-pyridin-2-ylmethyl)-1-benzyl-pyrrolidin-3-ol hydrochloride salt (I-7)

[6-(4-Substituted amino-1-benzyl-pyrrolidin-3-ylmethyl)-pyridin-2-yl]-carbamic acid tert-butyl ester (0.0002 mol, I-5), such as 6-[1-benzyl-4-(3-phenyl-propylamino)-pyrrolidin-3-ylmethyl]-pyridin-2-yl}-carbamic acid tert-butyl ester, or [6-(1-benzyl-4-hydroxy-pyrrolidin-3-ylmethyl)-pyridin-2-yl]-carbamic acid tert-butyl ester I-3, was cooled by an ice-water bath under argon. A solution of 4M HCl in 1,4-dioxane was then added slowly with stirring. The ice-water bath was removed after 3 h, and the reaction mixture was stirred at room temperature overnight. After the completion of the reaction, liquids were evaporated under reduced pressure, and the residue was partitioned between water (10 mL) and ethyl acetate (10 mL). The aqueous layer was then washed with ethyl acetate (5 mL×2). After evaporation of water by high vacuum rotorvapor, the residue was dried by a lyophilizer to give the product.

Example 7

Various other compounds, including those of FIG. 1, were prepared in accordance with the synthetic route of Scheme I. All the chemical structures were confirmed by $^1$H NMR, $^{13}$CNMR, and mass spectra. All of the products are racemic mixtures.

Example 8

Without limitation, in accordance with Scheme I and compound I-6, compounds P-3 and P-5 of FIG. 1 were prepared as shown in Scheme Ia.

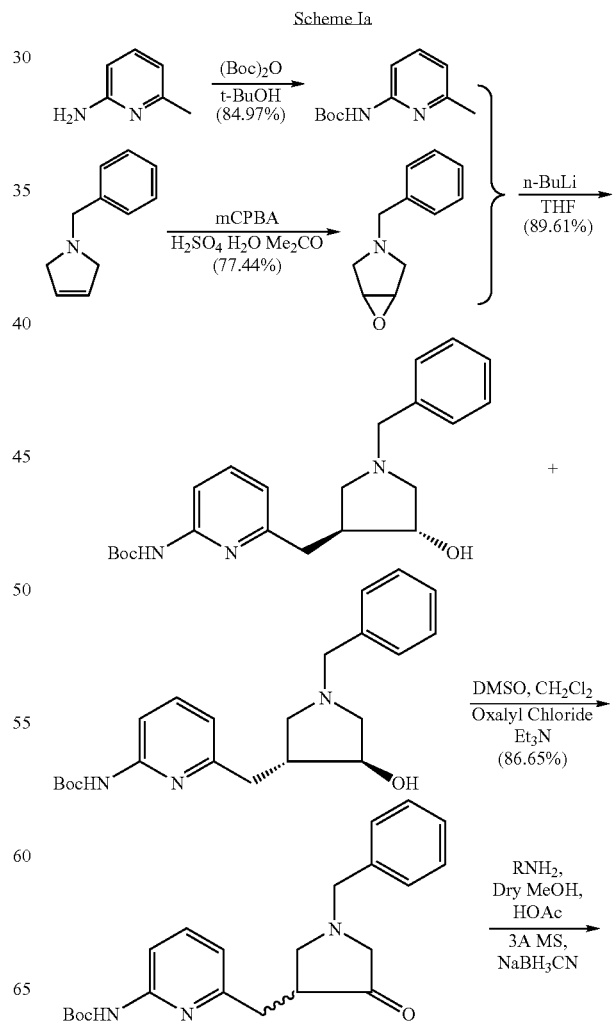

Scheme Ia

-continued
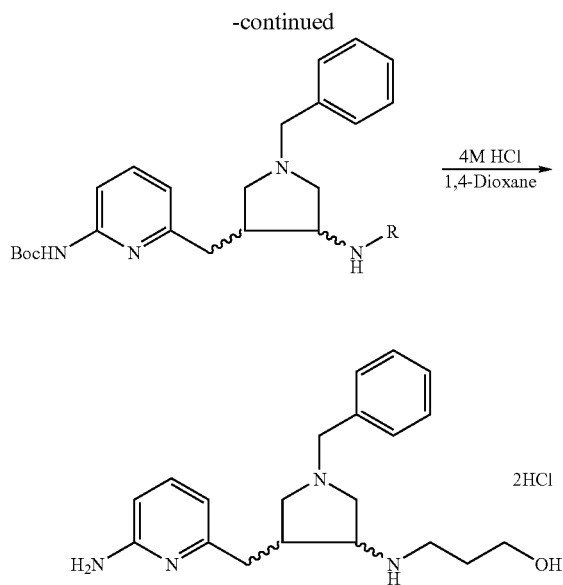
Examples 9-16 can be considered in conjunction with Scheme II, below.
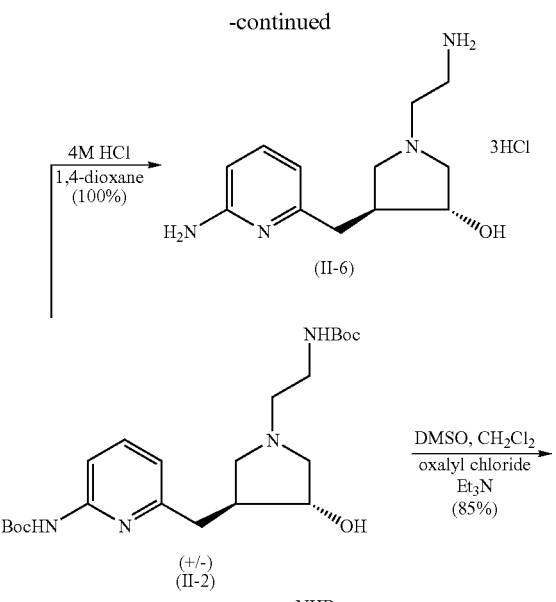
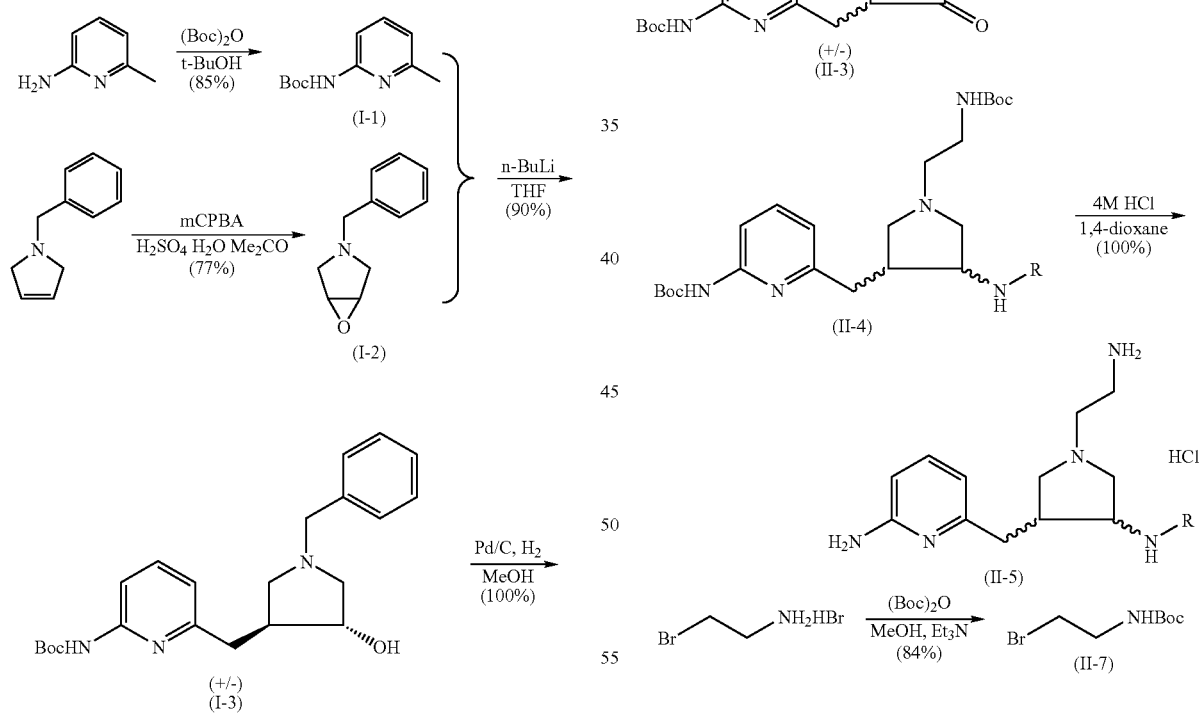
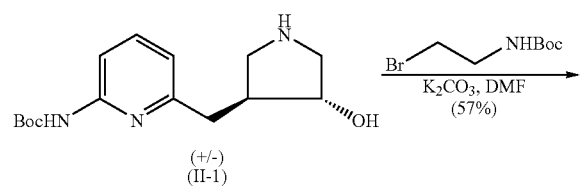
Example 9
Synthesis of [6-(4-hydroxy-pyrrolidin-3-ylmethyl)-pyridin-2-yl]-carbamic acid tert-butyl ester (II-1)
A suspension of [6-(1-benzyl-4-hydroxy-pyrrolidin-3-yl-methyl)-pyridin-2-yl]-carbamic acid tert-butyl ester I-3 (0.002 mol) and 10% Pd—C (0.7 g) in MeOH (30 mL) was stirred at 45° C. under hydrogen overnight. Then, the catalyst was removed by filtration and washed with MeOH (30 mL). The filtrate was concentrated to give II-1. Most of the product was used in the next reaction without further purification (100%). Some was purified by column chromatography (silica gel, $CH_2Cl_2$:MeOH:$Et_3N$, 6:30:0.1) to determine NMR and mass spectrum.

Example 10

Synthesis of {6-[1-(2-tert-butoxycarbonylamino-ethyl)-4-hydroxy-pyrrolidin-3-ylmethyl]-pyridin-2-yl}-carbamic acid tert-butyl ester (II-2)

A mixture of [6-(4-hydroxy-pyrrolidin-3-ylmethyl)-pyridin-2-yl]-carbamic acid tert-butyl ester II-1 (0.01 mol), (2-bromo-ethyl)-carbamic acid tert-butyl (0.012 mol), anhydrous $K_2CO_3$ (0.02 mol) in 50 mL anhydrous DMF was stirred at room temperature overnight. Solids were filtered off. The filtrate was evaporated under reduced pressure. The residue was partitioned between EtOAc and water. The organic layer was washed with brine, dried over anhydrous $Na_2SO_4$, and evaporated in vacuo. The obtained residue was purified by column chromatography (silica gel, $CH_2Cl_2$: MeOH, 9:1). (57%)

Example 11

The synthetic procedure for {6-[1-(2-tert-butoxycarbony-lamino-ethyl)-4-oxo-pyrrolidin-3-ylmethyl]-pyridin-2-yl}-carbamic acid tert-butyl ester (II-3) is analogous to that of [6-(1-benzyl-4-oxo-pyrrolidin-3-ylmethyl)-pyridin-2-yl]-carbamic acid tert-butyl ester (I-4).

Example 12

The synthetic procedure for {6-[4-substituted amino-1-(2-tert-butoxycarbonylamino-ethyl)-pyrrolidin-3-ylmethyl]-pyridin-2-yl}-carbamic acid tert-butyl ester (II-4) is analogous to that for [6-(4-substituted amino-1-benzyl-pyrrolidin-3-ylmethyl)-pyridin-2-yl]-carbamic acid tert-butyl ester (I-5).

Example 13

The synthetic procedure for 6-[4-substituted amino-1-(2-amino-ethyl)-pyrrolidin-3-ylmethyl]-pyridin-2-ylamine hydrochloride salt (II-5) is analogous to that for 6-[1-benzyl-4-(substituted amino)-pyrrolidin-3-ylmethyl]-pyridin-2-ylamine hydrochloride salt (I-6).

Example 14

The synthetic procedure for 1-(2-amino-ethyl)-4-(6-amino-pyridin-2-ylmethyl)-pyrrolidin-3-ol hydrochloride salt (II-6) is analogous to that for 4-(6-amino-pyridin-2-ylm-ethyl)-1-benzyl-pyrrolidin-3-ol hydrochloride salt (I-7).

Example 15

Synthesis of (2-bromo-ethyl)-carbamic acid tert-butyl ester (II-7)

To a solution of 2-bromoethylamine hydrobromide (0.0049 mol) in MeOH (30 mL), triethylamine (7 mL) and di-tert-butyl dicarbonate (0.0098 mol) was added. The reaction mixture was stirred at 60° C. for 1 h and then at room temperature for 14 h. The reaction mixture was concentrated in vacuo, and then dissolved in $CH_2Cl_2$, washed successively with 1M HCl, brine, saturated $NaHCO_3$ aqueous solution and brine, dried over anhydrous $MgSO_4$ and concentrated in vacuo. The residue was purified by column chromatography (silica gel, 100% $CH_2Cl_2$) to give pure product as colorless oil (84%).

Example 16

Figure 2:
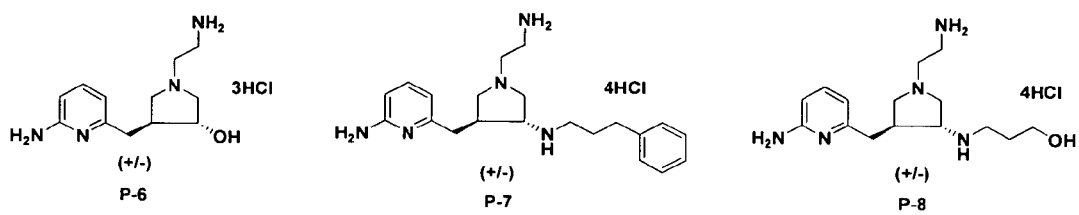
Figure 2:
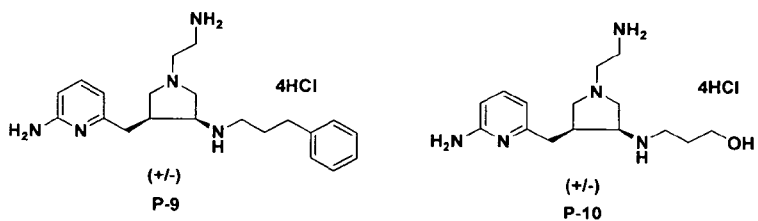

Various other compounds, including those of FIG. 2, were prepared in accordance with the synthetic route of Scheme II. All the chemical structures were confirmed by $^1$H NMR, $^{13}$CNMR, and mass spectra. All of the products are racemic mixtures.

Example 17

In accordance with Scheme II and compound II-5, compounds P-7 and P-9 of FIG. 2 were prepared as provided in Scheme IIa.

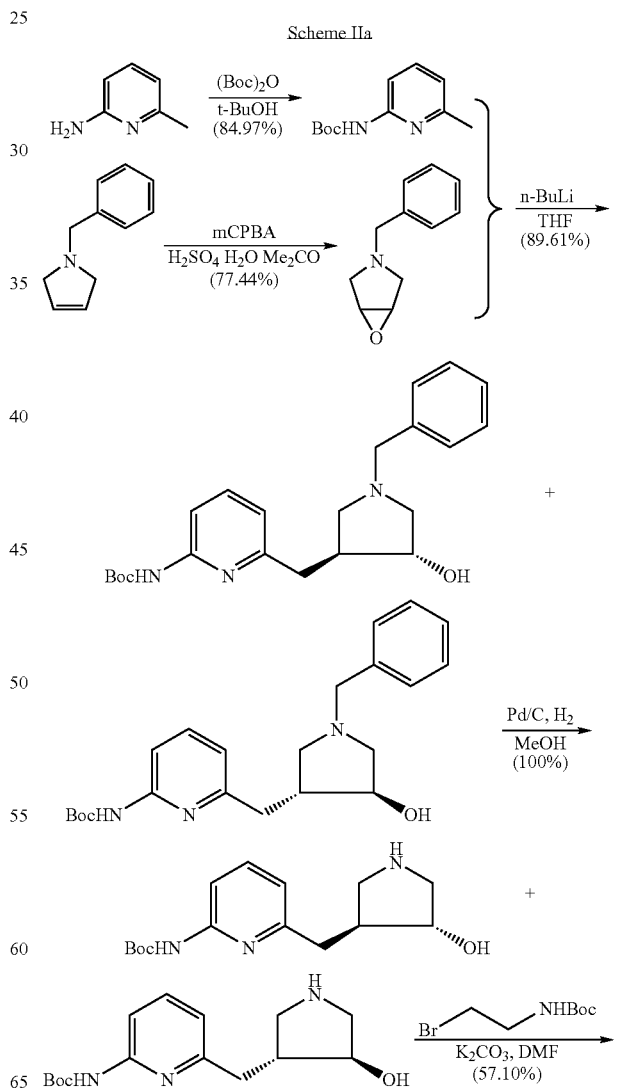

Scheme IIa

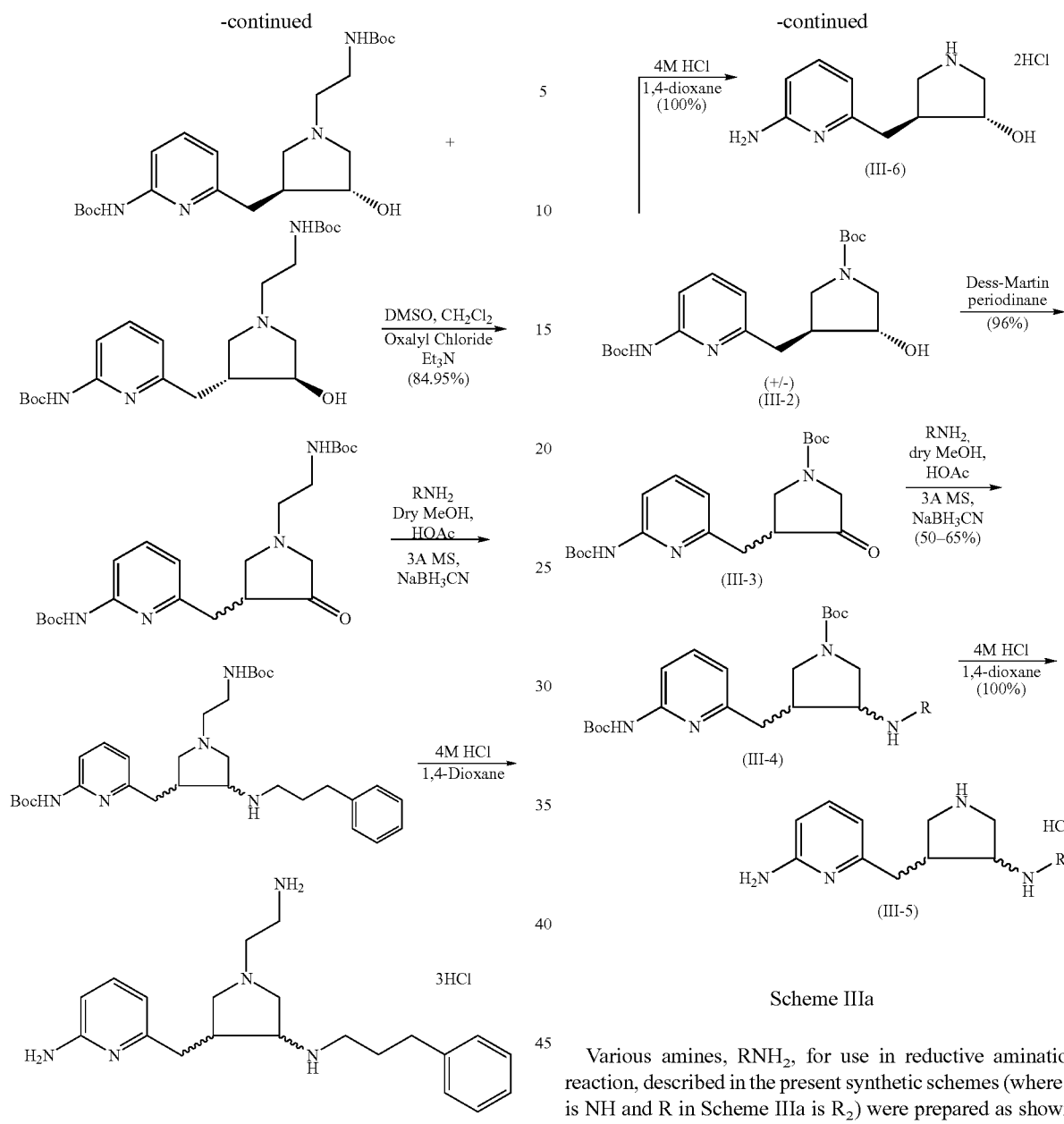

Examples 18-29 can be considered in conjunction with Schemes III and IIIa.

Various amines, RNH$_2$, for use in reductive amination reaction, described in the present synthetic schemes (where Z is NH and R in Scheme IIIa is R$_2$) were prepared as shown. With choice of starting aminoalcohol and/or reagent, each of the benzyl groups of compounds III-8 to III-13 can be, alternatively, substituted at any of the para, meta or ortho positions with a substituent including but not limited to halogen, alkyl or halogenated alkyl. Likewise, via such amines and reductive amination of an oxopyrrolidinyl intermediate, any of the benzyl groups of the compounds of FIG. 3 can be substituted.

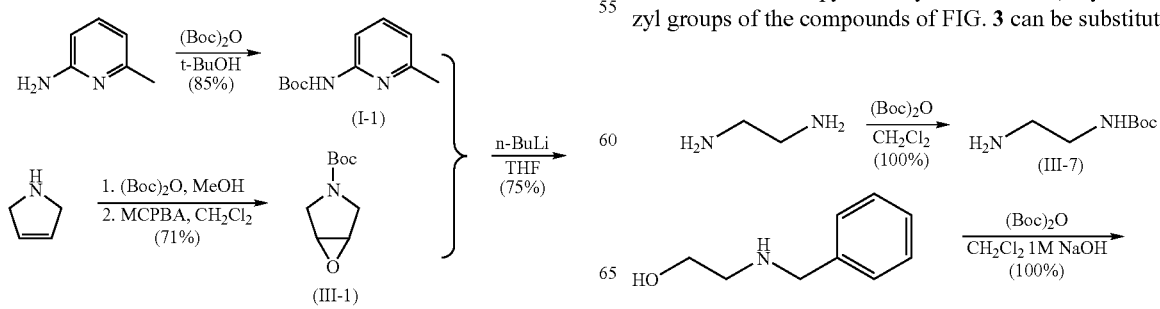

-continued

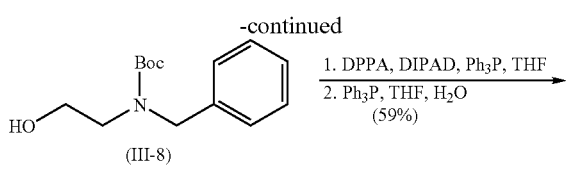

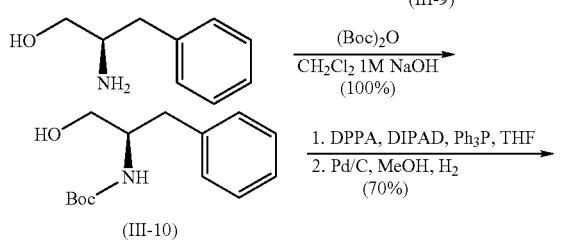

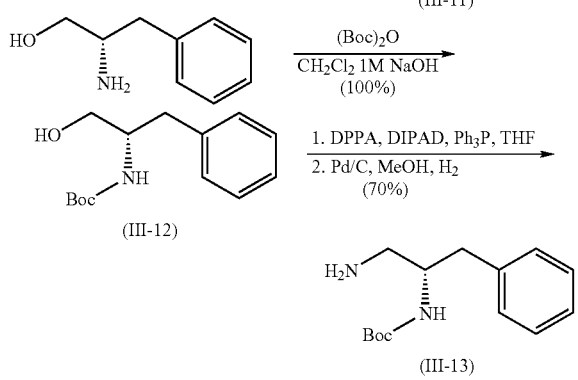

Example 18

Synthesis of 6-oxa-3-aza-bicyclo[3.1.0]hexane-3-carboxylic acid tert-butyl ester (III-1)

Di-Tert-Butyl Dicarbonate (0.015 Mol) was Added in Portions to a Solution of 3-pyrroline (0.01 mol, 65% pure) in 20 mL MeOH at 0° C. The reaction mixture was then stirred at room temperature for 24 h. (TLC monitored using 9:1 hexanes/EtOAc). After evaporation of the solvent, the residue was dissolved in 30 mL CH$_2$Cl$_2$. The reaction mixture was cooled to 0° C. and m-CPBA (0.013 mol, maximum 77% pure) was added in portions. After stirring the mixture at room temperature for 48 h, 20% Na$_2$SO$_3$ was added and two layers were separated. The aqueous layers were extracted with CH$_2$Cl$_2$ (20 mL×2). The combined organic extracts were washed with 20% Na$_2$SO$_3$ (30 mL×2) and water (30 mL×2). The solvent was then removed in vacuo. The residue was purified by column chromatography (silica gel, hexanes:EtOAc, 7:3) to give pure product (71%).

Example 19

The synthetic procedure for 3-(6-tert-butoxycarbonylamino-pyridin-2-ylmethyl)-4-hydroxy-pyrrolidine-1-carboxylic acid tert-butyl ester (III-2) is analogous to that for [6-(1-benzyl-4-hydroxy-pyrrolidin-3-ylmethyl)-pyridin-2-yl]-carbamic acid tert-butyl ester (I-3).

Example 20

Synthesis of 3-(6-tert-butoxycarbonylamino-pyridin-2-ylmethyl)-4-oxo-pyrrolidine-1-carboxylic acid tert-butyl ester (III-3)

To a suspension of Dess-Martin periodinane (0.0014 mol) in 10 mL CH$_2$Cl$_2$ was added a solution of 3-(6-tert-butoxycarbonylamino-pyridin-2-ylmethyl)-4-hydroxy-pyrrolidine-1-carboxylic acid tert-butyl ester III-2 (0.001 mol) in 5 mL CH$_2$Cl$_2$ and the reaction mixture was stirred at room temperature for 18 h. 1 M Na$_2$S$_2$O$_3$ (10 mL) was added to the reaction, and after stirring for 10 min, the reaction mixture was extracted with CH$_2$Cl$_2$(10 mL×3). The combined organic layers were washed with 5% aqueous NaHCO$_3$ (20 mL×3) and brine (20 mL×2). The organic layer was dried over anhydrous Na$_2$SO$_4$. The solvent was evaporated under reduced pressure. The residue was purified by column chromatography (silica gel, hexanes:EtOAc, 8:2) to give pure product (96%).

Example 21

The synthetic procedure for 3-substituted amino-4-(6-tert-butoxycarbonylamino-pyridin-2-ylmethyl)-pyrrolidine-1-carboxylic acid tert-butyl ester (III-4) is analogous to that for [6-(4-substituted amino-1-benzyl-pyrrolidin-3-ylmethyl)-pyridin-2-yl]-carbamic acid tert-butyl ester (I-5).

Example 22

The synthetic procedure for 6-(4-substituted amino-pyrrolidin-3-ylmethyl)-pyridin-2-ylamine (III-5) is analogous to that for 6-[1-benzyl-4-(substituted amino)-pyrrolidin-3-ylmethyl]-pyridin-2-ylamine (I-6).

Example 23

The synthetic procedure for 4-(6-amino-pyridin-2-ylmethyl)-pyrrolidin-3-ol hydrochloride salt is analogous to that for 4-(6-amino-pyridin-2-ylmethyl)-1-benzyl-pyrrolidin-3-ol hydrochloride salt (I-7).

Example 24

Synthesis of (2-amino-ethyl)-carbamic acid tert-butyl ester (III-7)

A solution of di-tert-butyl dicarbonate (0.01 mol) in dichloromethane (120 mL) was added dropwise to a solution of ethylenediamine (0.06 mol) in 30 mL dichloromethane over 5 h with vigorous stirring. Stirring was continued for a further 24 h at room temperature. After concentration to an oily residue, the reaction mixture was dissolved in aqueous 2M sodium carbonate (60 mL) and extracted with dichloromethane (30 mL×3). The organic layer was washed with 2M sodium carbonate (40 mL×2), and dried over anhydrous MgSO$_4$. The solvent was evaporated under reduced pressure to yield pure product (100%).

Example 25

Synthesis of benzyl-(2-hydroxy-ethyl)-carbamic acid tert-butyl ester (III-8)

A solution of di-tert-butyl dicarbonate (0.01 mol) in CH$_2$Cl$_2$ (15 mL) was added dropwise to a solution of 2-benzylamino-ethanol (0.01 mol) in 15 mL of CH$_2$Cl$_2$ and 12 mL of 1M NaOH. After stirring 24 h at room temperature, the organic layer was separated, washed with water (25 mL×2) and dried over anhydrous Na$_2$SO$_4$, Removal of solvent under reduced pressure give crude product as an oil, which was purified by column chromatography (silica gel, hexanes: EtOAc, 7:3) (100%).

Example 26

Synthesis of (2-amino-ethyl)-benzyl-carbamic acid tert-butyl ester (III-9)

Triphenylphosphine (0.0125 mol) in dry THF (10 mL) was added to benzyl-(2-hydroxy-ethyl)-carbamic acid tert-butyl ester III-8 in THF (30 mL) at 0° C. under nitrogen via a cannula. Diisopropyl azodicarboxylate (DIPAD) (0.013 mol) was then added dropwise and the solution was stirred for 20 min at 0° C. after the addition of DIPAD. Diphenyl phosphonic azide (DPPA) (0.0125 mol) was added at 0° C. and the solution was stirred for 5 h at room temperature (TLC monitor the amount of III-8). The solution was then concentrated in vacuo and the crude residue was purified by column chromatography to yield azide intermediate (silica gel, hexanes: EtOAc, 9.5:0.5).

To a solution of above azide intermediate in THF (5 mL) were added Ph$_3$P (0.012 mol) and water (0.03 mol) at 0° C. The mixture was stirred 2 h at 0° C. and 21 h at room temperature. The solvent was removed under reduced pressure, and the residue was treated with 10% citric acid (30 mL) and EtOAc (15 mL). The aqueous layer separated was washed EtOAc (10 mL×2). Then the aqueous layer was basified with 2M NaOH and the alkaline solution was extracted with CH$_2$Cl$_2$ (30 mL×3). The extracts were dried over anhydrous MgSO$_4$, and the solvent was then removed under reduced pressure to give pure product.

Example 27

The synthetic procedure for (2R)-2-N-Boc-amino-3-phenyl-1-propanol (III-10) and (2S)-2-N-Boc-amino-3-phenyl-1-propanol (III-12) is analogous to that for benzyl-(2-hydroxy-ethyl)-carbamic acid tert-butyl ester (III-8).

Example 28

Synthesis of (2R)-2-N-Boc-3-phenyl-propane-1,2-diamine (III-11) or (2S)-2-N-Boc-3-phenyl-propane-1,2-diamine (III-13)

Triphenylphosphine (0.0125 mol) in dry THF (10 mL) was added to 2-N-Boc-amino-3-phenyl-1-propanol (III-10 or III-12) in THF (30 mL) at 0° C. under nitrogen via a cannula. Diisopropyl azodicarboxylate (DIPAD) (0.013 mol) was then added dropwise, and the solution was stirred for 20 min at 0° C. after the addition of DIPAD. Diphenyl phosphonic azide (DPPA) (0.0125 mol) was added at 0° C., and the solution was stirred for 5 h at room temperature (TLC monitor the amount of III-10, or III-12). The solution was then concentrated in vacuo and the crude residue was purified by column chromatography to yield azide intermediate (silica gel, hexanes: EtOAc, 9.5:0.5).

The above azide intermediate was dissolved in 10 ml MeOH containing a catalytic amount of 10% Pd/C (0.5 g). The solution was stirred under a H$_2$ atmosphere at room temperature for 24 h. The solution was then filtered through Celite, and the filtrate was concentrated in vacuo. The residue was treated with 10% citric acid (30 mL) and EtOAc (15 mL). The aqueous layer separated was washed EtOAc (10 mL×2). Then the aqueous layer was basified with 2M NaOH and the alkaline solution was extracted with CH$_2$Cl$_2$ (30 mL×3). The extracts were dried over anhydrous MgSO$_4$, and the solvent was then removed under reduced pressure to give pure product.

Example 29

Figure 3:
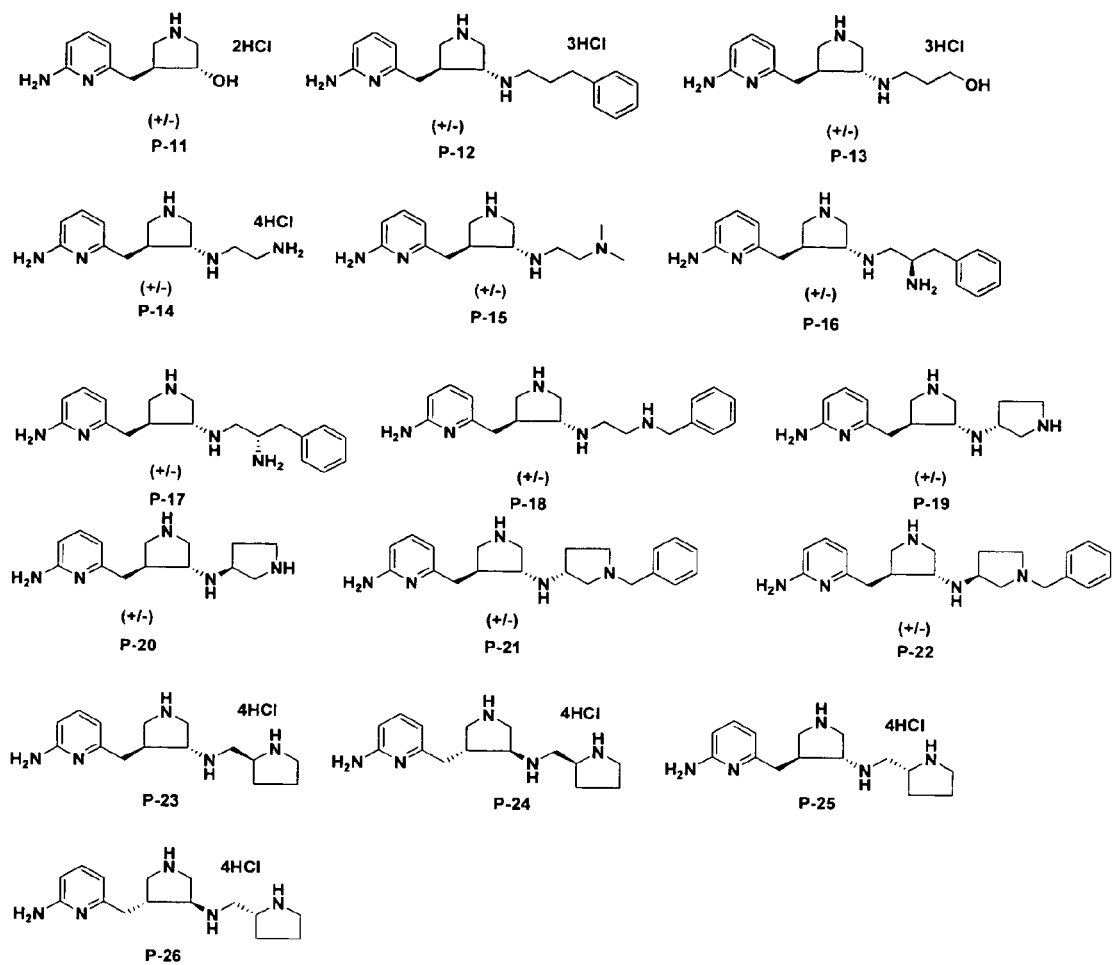
Figure 4:
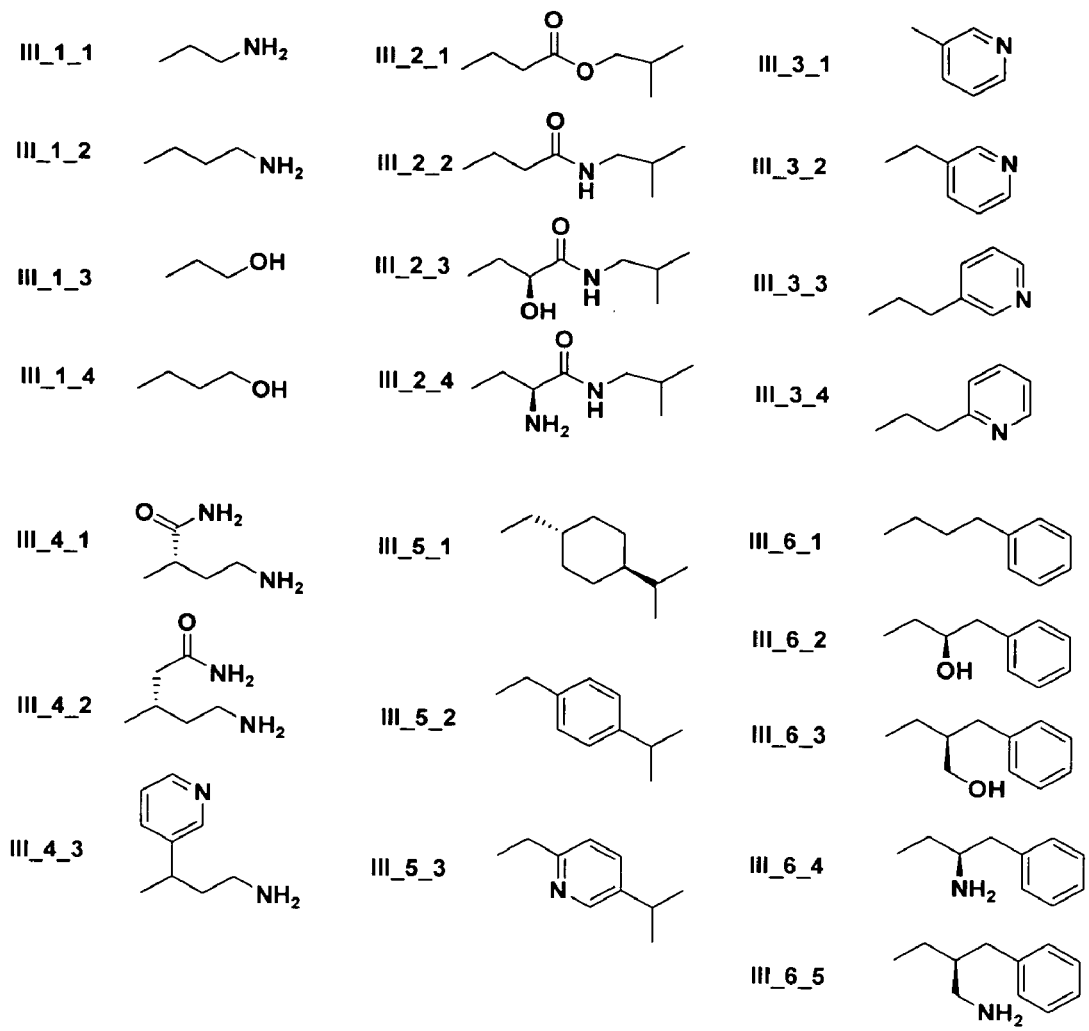
FIG. 4 provides, without limitation, various R$_2$ moieties corresponding to substructure III of compounds in accordance with this invention.

Various other compounds, including those of FIG. 3, were prepared in accordance with the synthetic routes of Schemes III and IIIa. (Other R$_2$ moieties corresponding to substructure III, whether Z is NH or O, are provided in FIG. 4.) All the chemical structures were confirmed by $^1$H NMR, $^{13}$CNMR, and mass spectra. All of the products, except P-23 through P-26, and P-36 through P-43, are racemic mixtures.

Example 30

In accordance with Scheme III and compound III-5, compounds P-13 and P-38 of FIG. 3 were prepared as shown in Scheme IIIb, below.

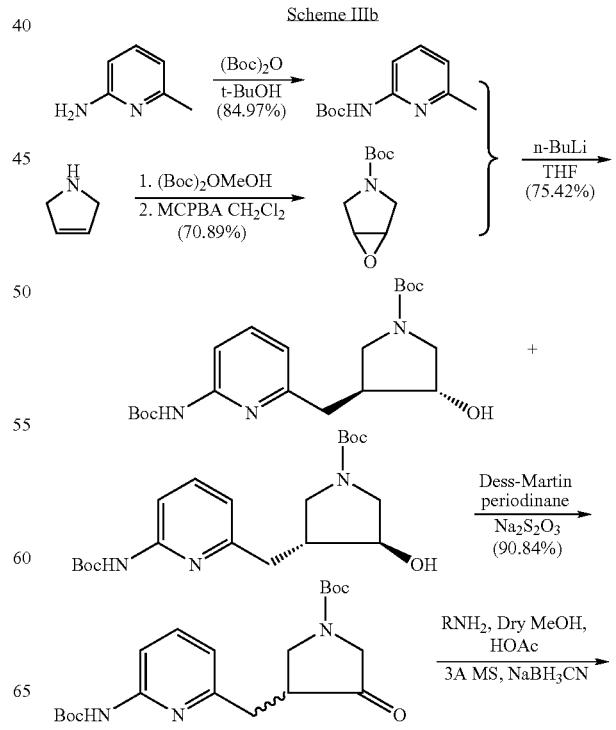

Scheme IIIb

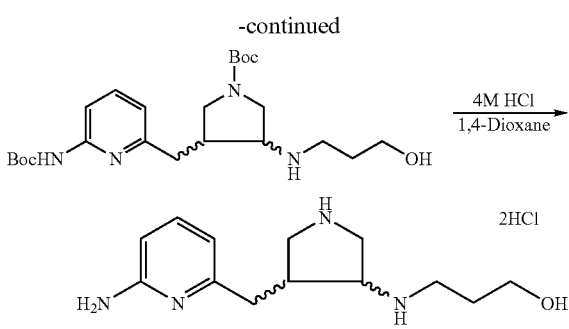

Examples 31-38 can be considered in conjunction with Scheme IV, below.

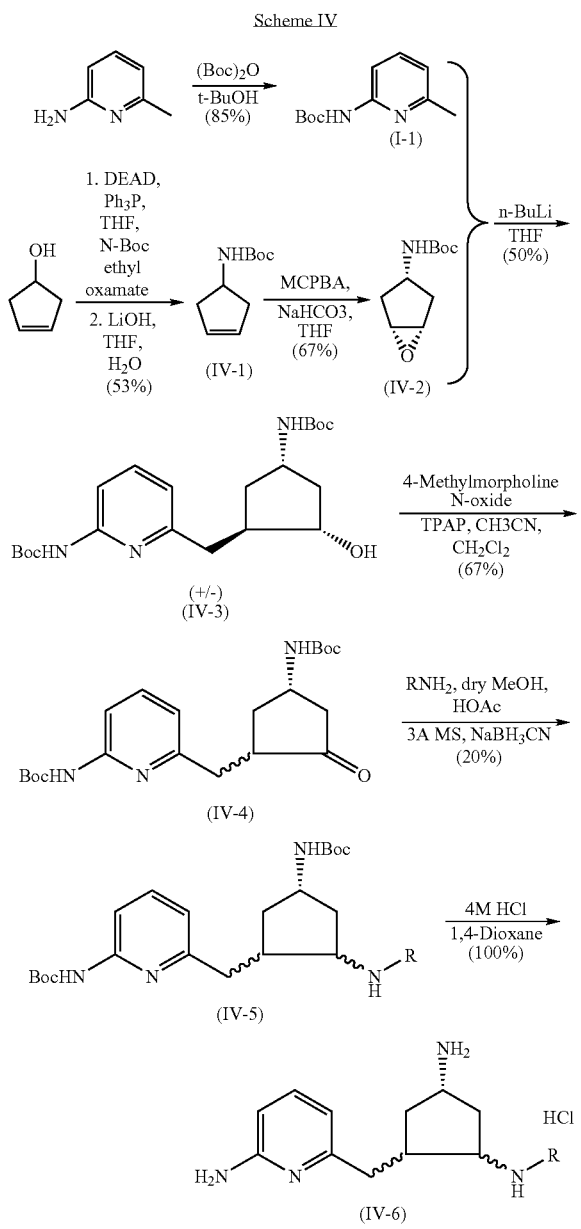

Example 31

Synthesis of cyclopent-3-enyl-carbamic acid tert-butyl ester (IV-1)

To a 3-necked round bottom flask cooled in an ice-water bath was added a solution of $Ph_3P$ (0.015 mol) in anhydrous THF (10 mL), a solution of 3-cyclopenten-1-ol (II) (0.012 mol) in anhydrous THF (10 mL), and a solution of N-Boc ethyl oxamate (0.015 mol) in anhydrous THF (10 mL). DEAD (0.015 mol) was then added dropwise to the above mixture. The reaction mixture was stirred at 0° C. for 2 h, and then allowed to react at room temperature for 48 h. The solvent was removed in vacuo and the residue was dissolved in $CH_2Cl_2$ (30 mL), and washed with water and brine (20 mL×3). The solvent was removed in vacuo, and the residue was purified by column chromatography (silica gel, 100% dichloromethane) to yield a mixture of product, (tert-butoxycarbonyl-cyclopent-3-enyl-amino)-oxo-acetic acid ethyl ester, and N-Boc ethyl oxamate that was used without further purification.

To a stirred solution cooled in an ice-water bath of the above crude product, (tert-butoxycarbonyl-cyclopent-3-enyl-amino)-oxo-acetic acid ethyl ester, (3.80 g) in THF (35 mL) was added a solution of LiOH (0.0765 mol) in water (35 mL). The mixture was stirred in the ice-water bath for 3 h. The organic material was extracted with $CH_2Cl_2$ (30 mL×3), the organic layers were combined and washed with brine (30 mL×2), and the solvent was removed in vacuo. The residue was purified by column chromatography (silica gel, 100% dichloromethane) to obtain white crystals of pure product (53%).

Example 32

Synthesis of cis-(6-oxa-bicyclo[3.1.0]hex-3-yl)-carbamic acid tert-butyl ester (IV-2)

Solid $NaHCO_3$ (0.0167 mol) and m-CPBA (0.0128 mol) were added in portions to a stirred solution of cyclopent-3-enyl-carbamic acid tert-butyl ester IV-1 (0.0093 mol) in $CH_2Cl_2$ (60 mL). The mixture was stirred at 0° C. for the first 2 h of the reaction and then allowed to stir for about 48 h at room temperature. Aqueous 20% $Na_2SO_3$ (30 mL) was added, and the two layers were separated. The aqueous layer was extracted with $CH_2Cl_2$ (20 mL×3), and the combined organic layers were washed with 20% $Na_2SO_3$ (30 mL×1), 5% $NaHCO_3$ (30 mL×1), and water (30 mL×1). The combined organic phase was concentrated in vacuo, and the residue was purified by column chromatography (silica gel, 100% dichloromethane) to give pure product as a colorless oil (64%).

Example 33

Synthesis of [6-(4-tert-butoxycarbonylamino-2-hydroxy-cyclopentylmethyl)-pyridin-2-yl]-carbamic acid tert-butyl ester (IV-3)

A solution of (6-methyl-pyridin-2-yl)-carbamic acid tert-butyl ester I-1 (0.0028 mol) in THF (10 mL) was cooled to −78° C. under N$_2$. To the cooled solution, n-BuLi (1.6 M in hexanes, 0.0097 mol) was added dropwise over 50 min. The solution changed from colorless to orange, then to red. After being stirred for 30 min at −78° C. the solution was stirred at room temperature for 30 min at which point it became dark red. The reaction mixture was cooled to −78° C. and cis-(6-oxa-bicyclo[3.1.0]hex-3-yl)-carbamic acid tert-butyl ester IV-2 (0.0032 mol) was added over a period of 2 h. After addition was complete, the mixture was stirred at −78° C. for 2 h and then stirring continued at room temperature for 2 h. The reaction mixture was quenched with the addition of ice-water and was extracted with CH$_2$Cl$_2$ (20 mL×3). The combined organic layers were washed with brine (30 mL×1) and concentrated in vacuo. After column chromatography (silica gel, hexanes:EtOAc, 1:1), pure product was obtained as a white-yellow solid (50%).

Example 34

Synthesis of [6-(4-tert-butoxycarbonylamino-2-oxo-cyclopentylmethyl)-pyridin-2-yl]-carbamic acid tert-butyl ester (IV-4)

Tetrapropylammonium perruthenate (0.07 mmol, 5 mol %) was added to a stirred solution of [6-(4-tert-butoxycarbonylamino-2-hydroxy-cyclopentylmethyl)-pyridin-2-yl]-carbamic acid tert-butyl ester IV-3 (0.14 mmol) and N-methyl-morpholine-N-oxide (0.26 mmol) in dichloromethane (9 mL) and acteonitrile (1 mL) at room temperature, and was allowed to react overnight. When complete, the solvent was evaporated in vacuo and the residue was purified by column chromatography (silica gel, CH$_2$Cl$_2$:EtOAc, 8:2) to afford pure product as a white solid (67%).

Example 35

The synthetic procedure for [6-(2-substituted amino-4-tert-butoxycarbonylamino-cyclopentylmethyl)-pyridin-2-yl]-carbamic acid tert-butyl ester (IV-5) is analogous to that for [6-(4-substituted amino-1-benzyl-pyrrolidin-3-ylmethyl)-pyridin-2-yl]-carbamic acid tert-butyl ester (I-5).

Example 36

The synthetic procedure for 4-(6-amino-pyridin-2-ylmethyl)-N$^3$-substituted-cyclopentane-1,3-diamine (IV-6) is analogous to that for 6-[1-benzyl-4-(substituted amino)-pyrrolidin-3-ylmethyl]-pyridin-2-ylamine hydrochloride salt (I-6)

Example 37

Figure 5:
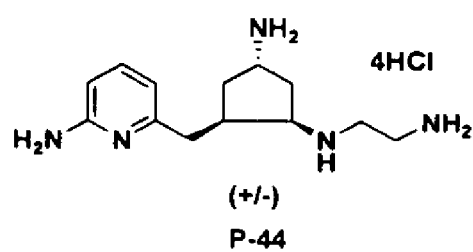
FIGS. 5 and 6 provide several cis and trans isomers of compounds in accordance with this invention.
Figure 5:
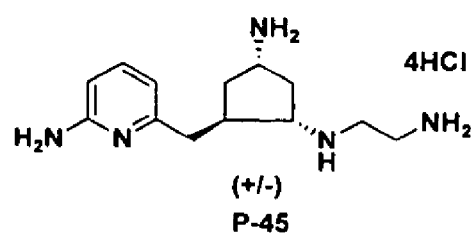

Various other compounds, including those of FIG. 5, were prepared in accordance with the synthetic route of Scheme IV. All of the chemical structures were confirmed by $^1$H NMR, $^{13}$CNMR, and mass spectra. All of the products are racemic mixtures.

Example 38

In accordance with Scheme IV and compound IV-6, compounds P-44 and P-45 of FIG. 5 were prepared as provided in Scheme IVa, below.

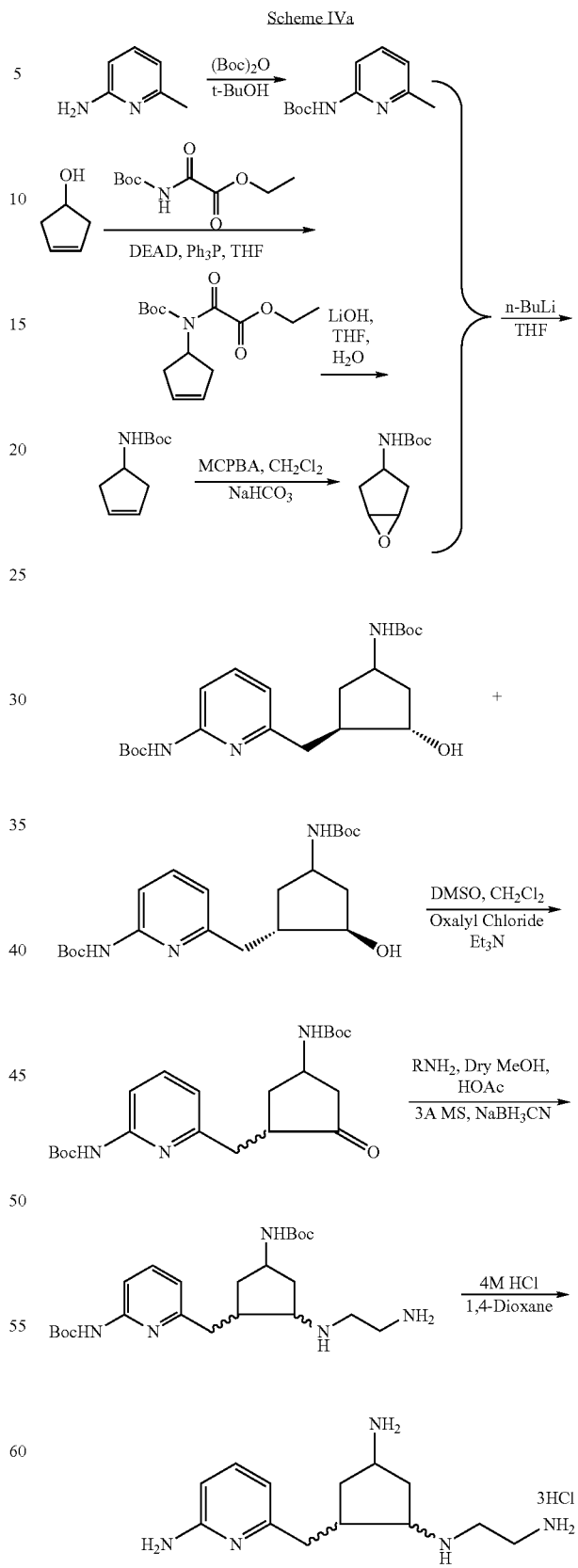

Examples 39-44 can be considered in conjunction with Scheme V, below.

Scheme V

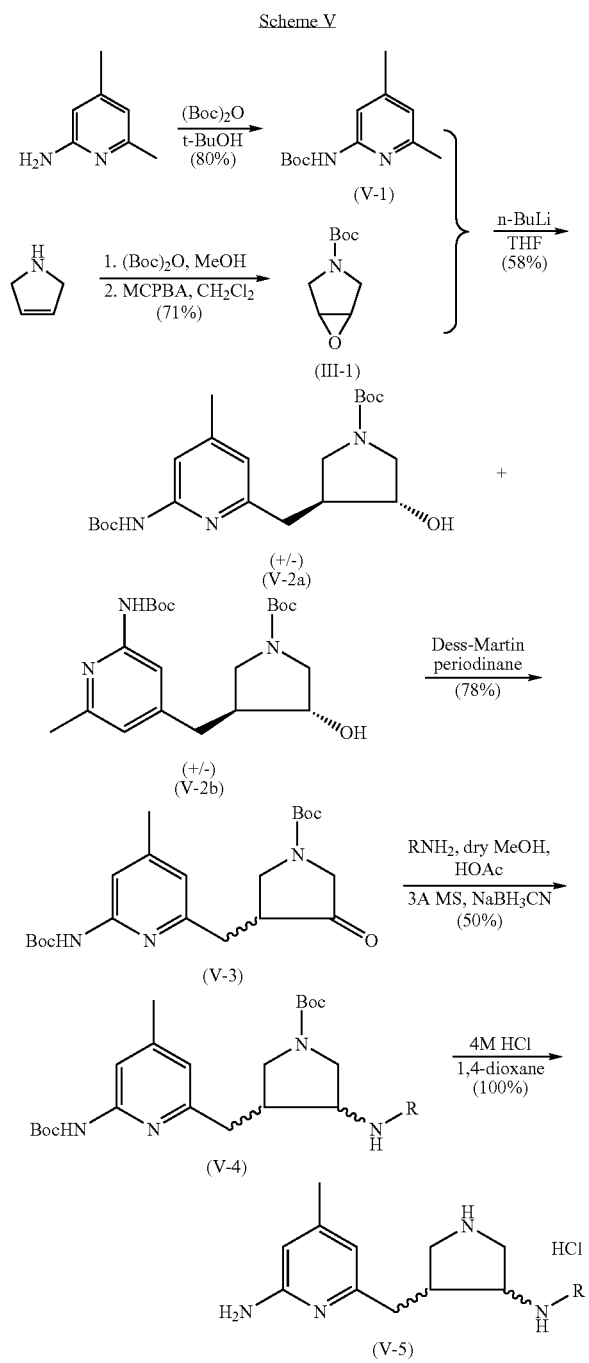

Example 39

The synthetic procedure for (4,6-dimethyl-pyridin-2-yl)-carbamic acid tert-butyl ester (V-1) is analogous to that for (6-methyl-pyridin-2-yl)-carbamic acid tert-butyl ester (I-1).

Example 40

Synthesis of 3-(6-tert-butoxycarbonylamino-4-methyl-pyridin-2-ylmethyl)-4-hydroxy-pyrrolidine-1-carboxylic acid tert-butyl ester (V-2a) and 3-(2-tert-butoxycarbonylamino-6-methyl-pyridin-4-ylmethyl)-4-hydroxy-pyrrolidine-1-carboxylic acid tert-butyl ester (V-2b).

A solution of (6-methyl-pyridin-2-yl)-carbamic acid tert-butyl ester I-1 (0.005 mol) in 20 mL THF was cooled in a −78° C. bath (dry ice in acetone). n-BuLi (1.6 M in hexanes, 0.0125 mol) was added during 15 min under $N_2$. The color of the solution changed from colorless to orange. Then the cooling bath was removed. After 30 min stirring at room temperature, the color solution changed to dark red. The solution was then returned to the −78° C. bath. 6-Oxa-3-aza-bicyclo[3.1.0]hexane-3-carboxylic acid tert-butyl ester III-1 (0.00625 mol) in 10 mL THF was added during 1 h. After 2 h, the cooling bath was removed. The solution was stirred for 2 h more at room temperature. The reaction was quenched by the addition of ice-cold water (50 ml). The mixture was extracted with $CH_2Cl_2$ (30 ml×3). The combined organic layers were washed with brine and dried over anhydrous $MgSO_4$. The solvent was removed in vacuo and the residue was purified by column chromatography (silica gel, hexanes:MeOH, 9:1) (58%). Two geometrical isomers V-2a and V-2b can be obtained by this eluent system. The molar ratio of V-2a and V-2b is 2:1.

Example 41

The synthetic procedure for 3-(6-tert-butoxycarbonylamino-4-methyl-pyridin-2-ylmethyl)-4-oxo-pyrrolidine-1-carboxylic acid tert-butyl ester (V-3) is analogous to that for 3-(6-tert-butoxycarbonylamino-pyridin-2-ylmethyl)-4-oxo-pyrrolidine-1-carboxylic acid tert-butyl ester (III-3).

Example 42

The synthetic procedure for 3-substituted amino-4-(6-tert-butoxycarbonylamino-4-methyl-pyridin-2-ylmethyl)-pyrrolidine-1-carboxylic acid tert-butyl ester (V-4) is analogous to that for [6-(4-substituted amino-1-benzyl-pyrrolidin-3-ylmethyl)-pyridin-2-yl]-carbamic acid tert-butyl ester (I-5).

Example 43

The synthetic procedure for 4-methyl-6-(4-substituted amino-pyrrolidin-3-ylmethyl)-pyridin-2-ylamine (V-5) is analogous to that for 6-[1-benzyl-4-(substituted amino)-pyrrolidin-3-ylmethyl]-pyridin-2-ylamine (I-6).

Example 44

Figure 6:
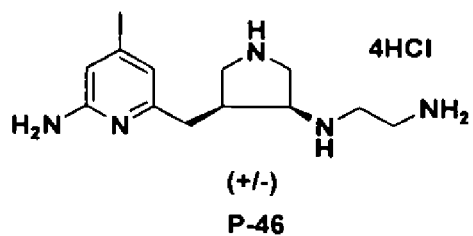
Figure 6:
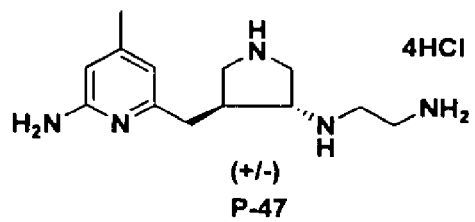

Various other compounds, including those of FIG. 6, were prepared in accordance with the synthetic route of Scheme V. All the chemical structures were confirmed by $^1$H NMR, $^{13}$CNMR, and mass spectra. All of the products are racemic mixtures.

Example 45 and compounds in accordance therewith can be considered in conjunction with Schemes VI-VII, below.

Scheme VI

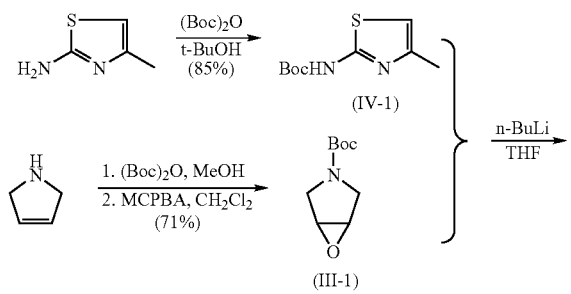

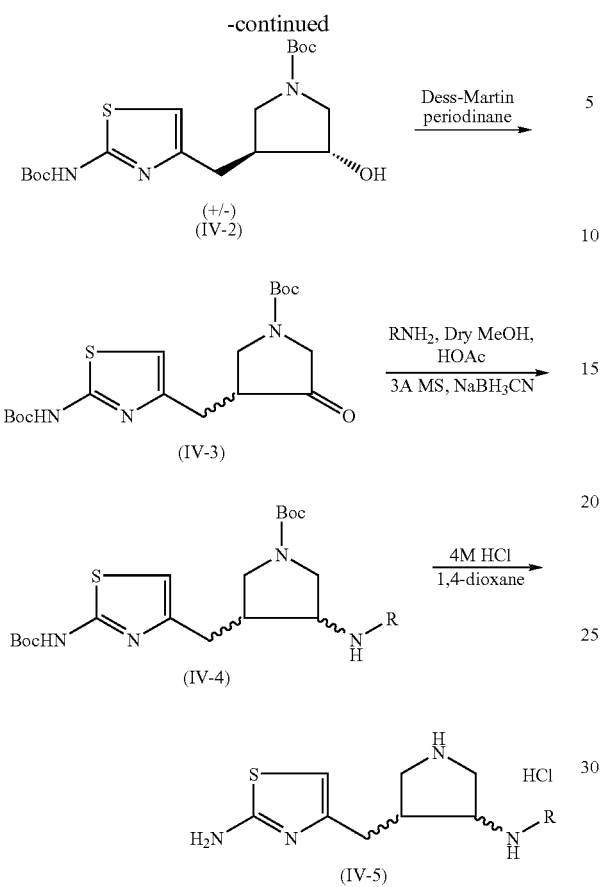

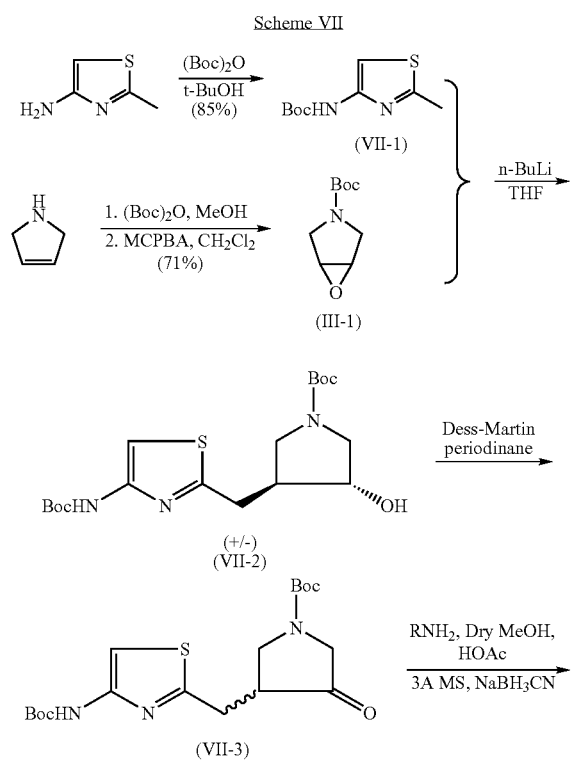

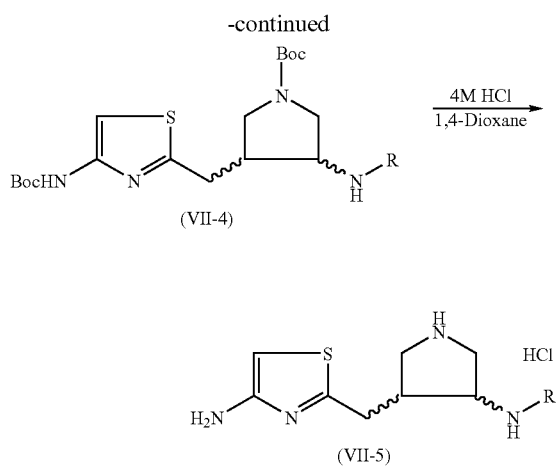

Example 45

Synthesis of (4-methyl-thiazol-2-yl)-carbamic acid tert-butyl ester (VII-1)

To a round bottom flask containing 40 mL $CH_2Cl_2$ was added 1 (695 mg, 6.09 mmol), 4-DMAP (52.3 mg, 0.43 mmol), and $Boc_2O$ (1.374 g, 6.29 mmol). The reaction mixture was stirred overnight at room temperature. Concentration of the solution in vacuo was followed by purification by column chromatography (silica gel, hexanes:EtOAc, 10:1), affording the product as white crystals (54%).

Example 46

In accordance with Scheme VI, various n-substituted pyrrolyl thiazoline compounds were prepared as provided in Scheme IVa, below.

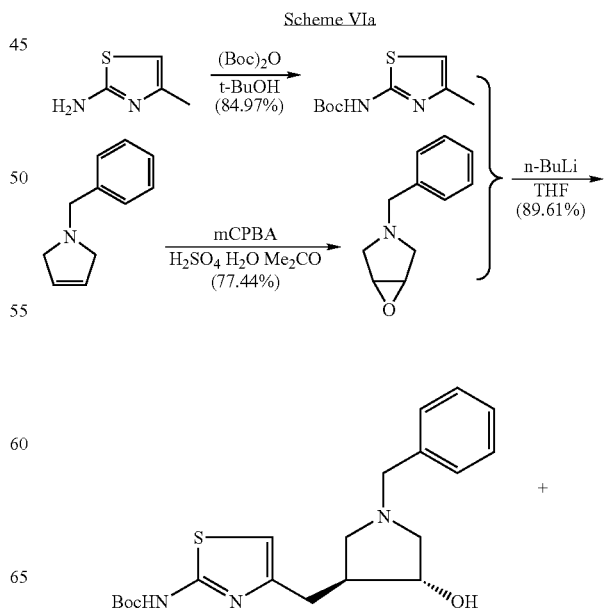

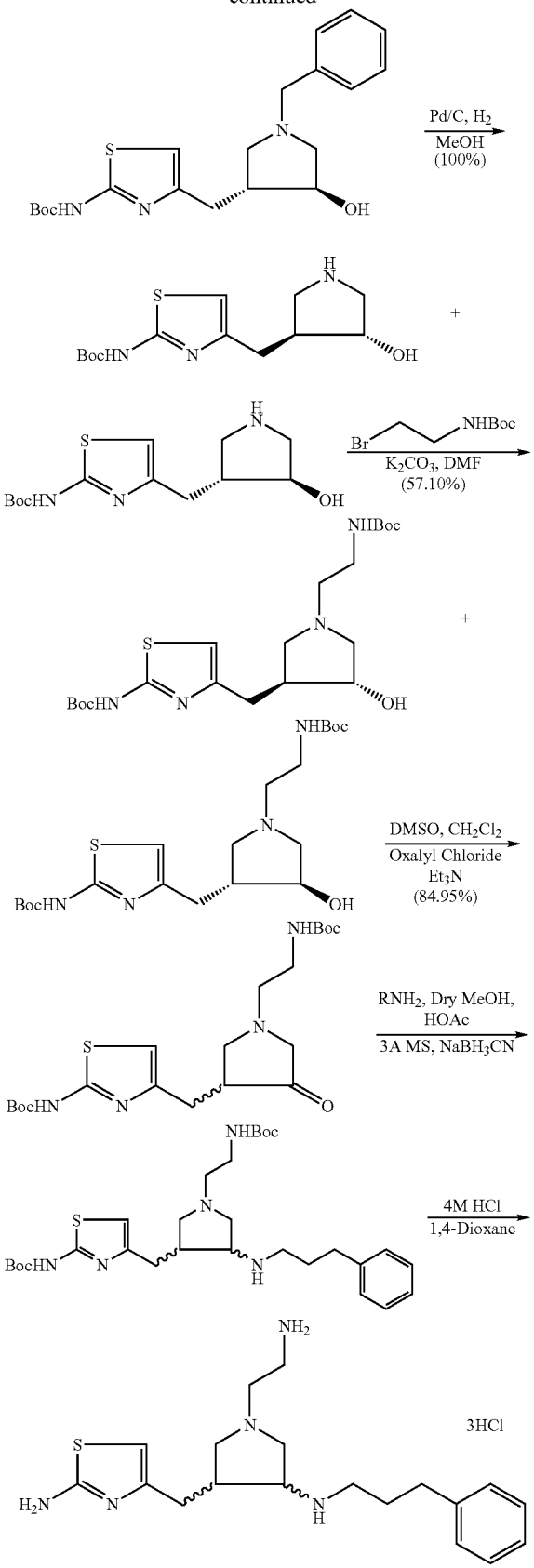

Examples 47 and 48 provide other synthetic procedures useful in the preparation of various compounds of this invention, as shown in Schemes I-VII.

Example 47

Synthesis of [6-(4-hydroxypyrrolidin-3-ylmethyl)-pyridin-2-yl]-carbamic acid tert-butyl ester, illustrating pyrrolidine reduction.

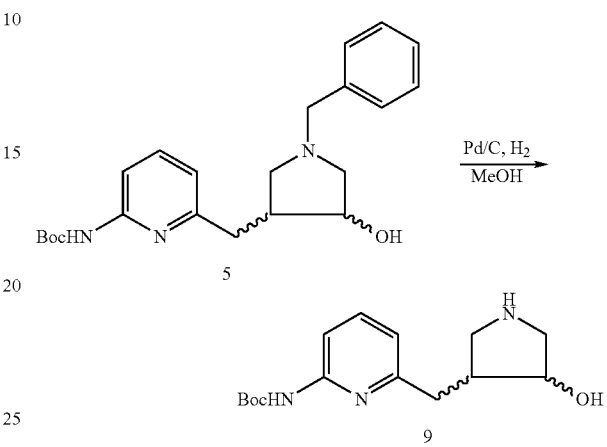

A suspension of 5 (0.002 mol) and 10% Pd—C (0.7 g) in MeOH (30 mL) was stirred at 45° C. under hydrogen (1 atm) for 7 h. Then the catalyst was removed by filtration and was washed with MeOH. The filtrate was concentrated to give 9 (100% yield). Most of the product was used in the next reaction without further purification. Some was purified by flash chromatography (silica gel, $CH_2Cl_2$:MeOH:$Et_3N$, 6:3:0.25) for structure analysis.

Example 48

Synthesis of 3-(6-tert-butoxycarbonylaminopyridin-2-ylmethyl)-4-oxo-pyrrolidine-1-carboxylic acid tert-butyl ester, illustrating pyrrolidine oxidation.

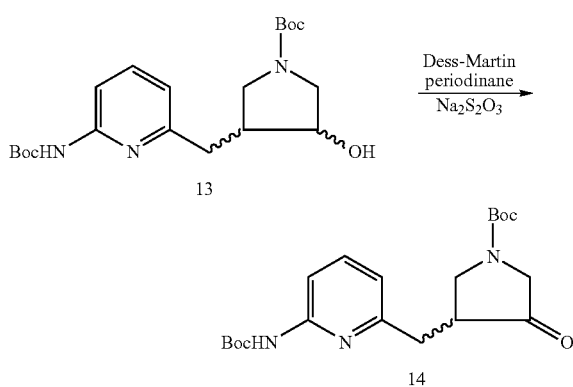

To a suspension of Dess-Martin periodinane (0.0014 mol) in 10 mL of $CH_2Cl_2$ was added a solution of 13 (0.001 mol) in 5 mL of $CH_2Cl_2$, and the reaction mixture was stirred at room temperature for 18 h. 1 M $Na_2S_2O_3$ (10 mL) was added to the reaction, and after stirring for 10 min the reaction mixture was extracted with $CH_2Cl_2$ (3×10 mL). The combined organic layers were washed with 5% aqueous $NaHCO_3$ (20 mL) and brine (20 mL). The organic layer was dried over $Na_2SO_4$ and evaporated. The mixture was purified by flash chromatography to give 14 in 96% yield (silica gel, $CH_2Cl_2$:EtOAc, 9.5:0.5).

Example 49

In accordance with the preceding, various other compounds can be prepared in an analogous fashion using comparable synthetic techniques or straightforward modifications thereof, as would be understood by those skilled in the art. For instance, compounds having substructure I comprising a thiazine (X=S, m=n=1), oxazine (X=O, m=n=1), pyrazine (X=N, m=n=1), oxazole (X=O, m=1 and n=0 or m=0 and n=1) or imidazole (X=N, m=1 and n=0 or m=0 and n=1) moiety can be prepared from the appropriate starting material using synthetic procedures of the sort described in Schemes I-VII. Likewise, compounds having substructure II comprising a cyclohexane (Y=CH, p=1, q=2 or p=2, q=1) or piperidine (Y=N, p=1, q=2 or p=2, q=1) moiety can be obtained using a suitable starting material. As would also be understood, any $R_2$ moiety of substructure III (Z=O or NH) can be introduced, limited only by the corresponding amine availability and its reactivity under the reductive amination conditions employed (Z=NH) or ether formation (Z=O) by alkylation of the corresponding alcohol directly after epoxide opening or after oxidation to the ketone followed by reduction and separation of the cis and trans alcohols.

Example 50

With regard to variation of substructure III, consider compounds in accordance with this invention, where $R_3$ can be a linear or cyclic aminoalkyl moiety. In particular, with reference to the compounds of this example, such moieties can comprise a benzyl group (X=H) or a substituted phenyl variation thereof (e.g., X can be but not limited to halogen, alkyl, or halogenated alkyl at any of the para, meta or ortho positions). Such compounds are prepared using an appropriate amine reagent (e.g., a substituted phenyl variation of amine III-9 in Scheme IIIa) for reductive amination of the corresponding oxopyrrolidinyl intermediate, in turn available via ring-opening reaction of lithiated 2-amino-4,6-dimethylpyridine with pyrroline epoxide, as demonstrated elsewhere herein.

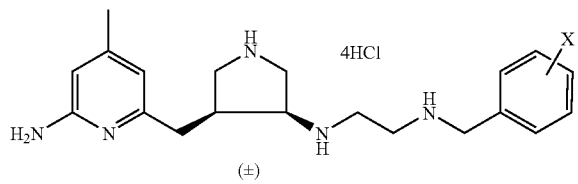

(±)

N-[4-(6-Amino-4-methyl-pyridin-2-ylmethyl)-pyrrolidin-3-yl]-N'-(2-,3-, or 4-Xbenzyl)-ethane-1,2-diamine

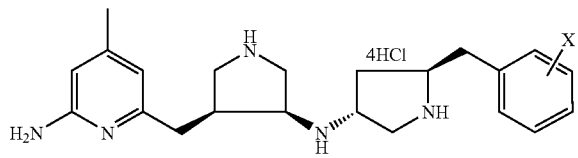

6-[4-(5-(2-, 3-, or 4-Xbenzyl-pyrrolidin-3-ylamino)-pyrrolidin-3-ylmethyl]-4-methyl-pyridin-2-ylamine

Example 51

Enzyme inhibitory assay. All of the NOS isoforms used are recombinant enzymes overexpressed in *E. coli* from different sources. The murine macrophage iNOS was expressed and purified according to the following procedure: (Hevel, J. M.; White, K. A.; Marletta, M. A. Purification of the Inducible Murine Macrophage Nitric Oxide Synthase. J. Biol. Chem. 1991, 266, 22789-22791.)

iNOS expression: An overnight culture of pCWiNOS was used to inoculate (1:100) larger cultures of Terrific Broth media (12 g/L tryptone, 24 g/L yeast extract, 4 mL/L glycerol, 17 mM $KH_2PO_4$, and 72 mM $K_2HPO_4$) containing 50 µg/mL ampicillin and 34 µg/mL chloramphenicol at 37° C. At an $OD_{600}$ of ~0.5, the culture was cooled to 25° C. and induced by the addition of 1 mM IPTG (final concentration). After approximately 24 h of growth at 25° C., the cells were pelleted at 5300×g, transferred to 50 mL conical tubes, and stored at −80° C.

iNOS purification: Cell pellets from 1.0 L of culture were resuspended in sonication buffer (50 mM Hepes, pH 7.4, 10% glycerol, 10 µg/mL benzamidine, 5 µg/mL leupeptin, 0.2 mM of PMSF, and 1 µg/mL each of pepstatin, chymostatin, and antipain) and lysed by sonication. Centrifugation for 20 min at 13000×g yielded supernatant which contained iNOS active enzyme. iNOS supernatant was loaded onto 1 g of a 2',5'-ADP-Sepharose 4B resin column. The column was then washed with 20 ml iNOS purification buffer (10 mM $K_2HPO_4$, 10% glycerol, 0.5 mM L-arginine, pH 7.4) and 10 µM $BH_4$. Inducible NOS was eluted with 30 ml iNOS purification buffer supplemented with 10 mM 2'(3')-AMP, 10 µM $BH_4$, and 0.3 M NaCl. The eluent was concentrated to 5 ml by ultrafiltration. The above concentration operation was repeated three times more with 10 ml Hepes buffer supplemented with 10 µM $BH_4$ to give purified inducible NOS.

Rat nNOS was expressed according to the procedure of Roman et al. (Roman, L. J.; Sheta, E. A.; Martasek, P.; Gross, S. S.; Liu, Q.; Masters, B. S. S. High-Level Expression of Functional Rat Neuronal Nitric Oxide Synthase in *Escherichia coli*. Proc. Natl. Acad. Sci. U.S.A. 1995, 92, 8428-8432.)

nNOS expression: An overnight culture of pCWnNOS was used to inoculate (1:100) larger cultures of Terrific Broth media (10 g/L tryptone, 20 g/L yeast extract, 4 ml/L glycerol, 19.5 mM $KH_2PO_4$, 30.5 mM $Na_2HPO_4$) containing 50 µg/mL ampicillin and 34 µg/mL chloramphenicol at 37° C. At an $OD_{600}$ of ~1.0, the culture was cooled 25° C. and induced by the addition of 0.5 mM IPTG, 450 µM d-aminolevulinic acid, 1 mM ATP, 3 µM riboflavin. After approximately 48 h of post-induction incubation in the dark at 25° C. the cells were pelleted at 5300×g, transferred to 50 mL conical tubes, and stored at −80° C.

The nNOS was purified according to the procedure of Gerber et al. (Gerber, N.C.; Montellano, P. R. Neuronal Nitric Oxide Synthase: Expression in *Escherichia coli*, Irreversible Inhibition by Phenyldiazene, and Active Site Topology. J. Biol. Chem. 1995, 270, 17791-17796).

nNOS purification: Cell pellets from 2.0 L of culture were resuspended in sonication Buffer A (50 mM Tris Base Buffer, pH 8.0, 10% glycerol), 2 mg/ml lysozyme. 0.5 mM L-arginine. 1 mM EDTA, 0.1 mM PMSF, 1 □g/ml antipain, and 1 µM each of leupeptin, pepstatin, and pepstatin) and lysed by sonication. Centrifugation for 1 h at 100000×g yielded supernatant which contained nNOS active enzyme. The supernatant was brought to 2 mM $CaCl_2$ and the protein was loaded onto a 15 ml calmodulin-Sepharose column equilibrated with Buffer A containing 2 mM $CaCl_2$. The column was washed with 100 ml Buffer B (50 mM Hepes, 5 mM DTT, and 10% DTT) containing 2 mM $CaCl_2$, 0.5 mM L-arginine, and 10 µM $BH_4$, and eluted with 30 ml Buffer B supplemented with 0.3 M NaCl, 5 mM EGTA, 0.5 mM L-arginine, and 10 µM $BH_4$. The protein was then loaded onto a 5 ml 2',5'-ADP-Sepharose column equilibrated with Buffer B supplemented with 0.3 M NaCl, 0.5 mM L-arginine, and 10 μM BH$_4$. The column was washed with 25 ml Buffer B containing 0.5 mM L-arginine and 10 μM BH$_4$, and then 25 ml of Buffer B only supplemented with 10 μM BH$_4$ (without L-arginine). Neuronal NOS was eluted with 20 ml Buffer B supplemented with 10 mM 2'(3')-AMP, 10 μM BH$_4$ and 0.3 M NaCl. The 20 ml eluent was then concentrated to 5 ml by ultrafiltration. The above concentration operation was repeated twice more with 10 ml Buffer B supplemented with 10 □M BH$_4$ to give the purified neuronal NOS.

Bovine eNOS was expressed and isolated by Martasek et al. (Martasek, P.; Liu, Q.; Roman, L. J.; Gross, S. S.; Sessa, W. C.; Masters, B. S. S. Characterization of Bovine Endothelial Nitric Oxide Synthase Expressed in *Escherichia coli*. Biochem. Biophys. Res. Commun. 1996, 219, 359-365). The procedure is below:

Expression of bovine eNOS: An overnight culture of BoveNOSpCW was used to inoculate 0.5 liter (in a 2.8-liter Fernbach flask) of modified TB (20 g of yeast extract, 10 g of bacto-tryptone, 2.65 g of KH$_2$PO$_4$, 4.33 g of Na$_2$HPO$_4$ and 4 ml of glycerol per liter) containing ampicillin (50 mg/ml) and chloramphenicol (35 mg/ml). The cultures were grown to an OD600 of z0.8 at 22° C. (200 rpm) and induced with 0.5 mM IPTG. One hour before IPTG induction, d-aminolevulinic acid (0.5 mM final) was added and, at the time of IPTG induction, riboflavin (3 mM final) and ATP (1 mM final) were also added. After induction, the flasks were kept in the dark at 22° C. (200 rpm). The cells were harvested 48 h after induction, and the cell pellet was frozen at −80° C. until purification was carried out.

Purification of bovine eNOS. The purification was typically carried out with eNOS from 2 liters of *E. coli* culture. The eNOS protein was purified using a modification of the published protocol for nNOS (14). The cells were resuspended in buffer C [50 mM Tris-Cl, pH 7.8, 1 mM EDTA, 1 mM DTT, 10% glycerol (v/v), 150 mM NaCl, 0.1 mM phenylmethylsulfonyl fluoride, 1 mM leupeptin and 1 mM pepstatin], lysed by pulsed sonication and then centrifuged to sediment the cell debris. The supernatant was applied to a 2',5'-ADP Sepharose 4B column equilibrated in buffer D [50 mM Tris-Cl, pH 7.8, 0.1 mM EDTA, 0.1 mM dithiothreitol, 150 mM NaCl, 10% glycerol (v/v)]. The column was washed with 20 column volumes of buffer B and again with 20 column volumes of buffer B containing 600 mM NaCl. Finally, protein was eluted with buffer B containing 600 mM NaCl and 5 mM 2'-AMP. The fractions were screened for absorption in the Soret region (A$_{400}$) and hemoprotein-containing fractions were pooled and concentrated (Centriprep 50, Amicon). Repeated dilution/concentration [50 mM Tris-Cl, pH 7.8, 0.1 mM EDTA, 0.1 mM dithiothreitol, 10% glycerol (vol/vol)] was used to reach a final concentration of 150 mM NaCl and commensurately reduce the 2'-AMP content. If harvested 24 h after IPTG induction, only a 47% yield was obtained relative to that after 48 h of IPTG treatment. The cytosolic extracts contained 6-10 mg of eNOS per liter, as determined by CO-difference spectra, and the 2',5'-ADP Sepharose 4B column pool yielded 3.6-6.0 mg (>>60% recovery). The purified eNOS is stored in the presence of 1 mM L-arginine.

eNOS washing: eNOS contains a significant amount of L-arginine, which will interfere with the enzyme assay. The L-arginine can be removed by several dilution and concentration steps using an Amico concentrator. The dilution buffer is 10 ml Tris-HCl 50 mM containing 0.1 mM EDTA, 400 mM NaCl, 10% glycerol and 1 mM beta-mercaptoethanol. The above dilution and concentration operation was repeated three times to give purified eNOS.

Nitric oxide formation from NOS was monitored by the hemoglobin capture assay as described previously. (Hevel, J. M.; Marletta, M. A. Nitric Oxide Synthase Assays. Methods Enzymol. 1994, 133, 250-258).

Procedure for iNOS: Into a disposable cuvette (1.5 ml) was added 10 μL of 0.6 mM L-arginine (the final concentration is 10 μM), 6 μL of inhibitor, 10 μL of 6.24 mM NADPH, 6 mL of 12.5 g/L hemoglobin-A0 (ferrous form), 6 μl of 1 mM BH$_4$, 556 μL of 100 mM Hepes buffer, 6 μL of iNOS, and the time-dependent increase in the 401 nm absorbance was monitored at 30° C.

Procedure for nNOS and eNOS: Into a disposable cuvette (1.5 ml) was added 10 μL of 0.6 mM L-arginine (the final concentration is 10 μM), 6 μL of inhibitor, 10 μL of 50 mM CaCl$_2$, 10 μL of 40,000 units/mL calmodulin, 10 μL of 6.24 mM NADPH, 6 μL of 12.5 g/L hemoglobin-A0 (ferrous form), 6 μl of 1 mM BH$_4$, 536 μL of 100 mM Hepes buffer, 6 μL of nNOS or eNOS, and the time-dependent increase in the 401 nm absorbance was monitored at 30° C. The IC$_{50}$ values were obtained by measuring the percentage of inhibition in the presence of 10 μM L-arginine with at least five concentrations of inhibitor. The apparent Ki values were calculated according to the following inhibition equation: % inhibition=100-[I]/{[I]+Ki(1+[S]/Km)} (Segel, I. H. Enzyme Kinetics; John Wiley and Sons: New York, 1975; p 105). The parameters of Km values for L-arginine were 1.3 μM (nNOS), 8.3 μM (iNOS), and 1.7 μM (eNOS). The selectivity of an inhibitor is defined as the ratio of the respective Ki values. The data of Table 1 show that the compounds of this invention inhibit NOS activity and selectively inhibit nNOS over other enzyme isoforms.

TABLE 1

The NOS enzyme assay results

| | IC$_{50}$(μM) | | | calc. Ki(μM) | | | Selectivity** | |
|---|---|---|---|---|---|---|---|---|
| | nNOS[a] | iNOS[b] | eNOS[c] | nNOS | iNOS | eNOS | n/i | n/e |
| P-1 | 682.33 | 2026.6 | | 78.5 | 919.16 | | 11.71 | |
| P-2 | 121.55 | 132.45 | | 13.98 | 60.07 | | 4.3 | |
| P-3 | 1654.48 | 3857.3 | | 190.34 | 1749.5 | | 9.19 | |
| P-4 | 416.75 | 1343.7 | | 47.94 | 609.43 | | 12.71 | |
| P-5 | 2650.77 | 5562.4 | | 304.96 | 2522.81 | | 8.27 | |
| P-6 | 108.17 | 230.71 | | 12.44 | 104.64 | | 8.41 | |
| P-7 | 34.61 | 965.19 | | 3.98 | 437.76 | | 109.99 | |
| P-8 | 117.1 | 1437.2 | | 13.47 | 651.85 | | 48.39 | |
| P-9 | 248.98 | 649.38 | | 28.64 | 294.53 | | 10.28 | |
| P-10 | 724.04 | 2756.9 | | 83.3 | 1250.38 | | 15.01 | |
| P-11 | 60.32 | 56 | 2345.69 | 6.94 | 25.24 | 340.83 | 3.64 | 49.11 |

TABLE 1-continued

The NOS enzyme assay results

| | IC$_{50}$(μM) | | | calc. Ki(μM) | | | Selectivity** | |
|---|---|---|---|---|---|---|---|---|
| | nNOS[a] | iNOS[b] | eNOS[c] | nNOS | iNOS | eNOS | n/i | n/e |
| P-12 | 115.47 | 317.07 | 586.35 | 13.28 | 143.81 | 85.20 | 10.83 | 6.42 |
| P-13 | 248.08 | 515.43 | 4705.49 | 28.54 | 233.77 | 683.70 | 8.19 | 23.96 |
| P-14 | 76.17 | 170.64 | 5961.51 | 8.76 | 77.39 | 866.20 | 8.83 | 98.88 |
| P-15 | 136.29 | 679.28 | 1663.47 | 15.68 | 308.09 | 241.7 | 19.65 | 15.41 |
| P-16 | 120.46 | 658.24 | >10,000* | 13.86 | 298.55 | >1,453 | 21.54 | >104.83 |
| P-17 | 178.79 | 918.56 | >10,000* | 20.57 | 416.61 | >1,453 | 20.25 | >70.64 |
| P-18 | 125.62 | 366.23 | >70,000* | 14.45 | 166.1 | >10.171 | 11.49 | >703.88 |
| P-19 | 181.9 | 558.76 | 3167.01 | 20.93 | 253.43 | 460.16 | 12.11 | 22.00 |
| P-20 | 111.66 | 516.05 | 4304.36 | 12.85 | 234.06 | 625.42 | 18.21 | 48.67 |
| P-21 | 212.14 | 629.56 | 1173.58 | 24.4 | 285.54 | 170.52 | 11.70 | 6.99 |
| P-22 | 155.74 | 460.84 | 748.02 | 17.92 | 209.01 | 108.69 | 11.66 | 6.07 |
| P-23 | 96.91 | 228.65 | | 11.15 | 103.7 | | 9.30 | |
| P-24 | 125.67 | 674.16 | | 14.46 | 305.77 | | 21.15 | |
| P-25 | 21.25 | 40.79 | | 2.44 | 18.5 | | 7.58 | |
| P-26 | 107.06 | 375.32 | | 12.32 | 170.23 | | 13.82 | |
| P-27 | 27.54 | 366.41 | 608.88 | 3.17 | 166.19 | 88.47 | 52.43 | 27.9 |
| P-28 | 82.07 | 315.45 | 2522.94 | 9.44 | 143.07 | 366.58 | 15.16 | 38.8 |
| P-29 | 3.38 | 128.76 | 2990.05 | 0.39 | 58.40 | 434.45 | 150.0 | 1114.0 |
| P-30 | 28.97 | 429.14 | 962.96 | 3.33 | 194.64 | 139.92 | 58.45 | 42.02 |
| P-31 | 21.04 | 524.33 | >10,000* | 2.42 | 237.81 | >1,453 | 98.27 | >600 |
| P-32 | 19.98 | 654.63 | >10,000* | 2.3 | 296.9 | >1,453 | 129.09 | >632 |
| P-33 | 10.22 | 354.75 | >70,000* | 1.18 | 160.9 | >10,171 | 136.36 | >8619.5 |
| P-34 | 10.95 | 383.54 | 1669.65 | 1.26 | 173.95 | 242.6 | 138.06 | 192.54 |
| P-35 | 11.79 | 440.03 | 2918.87 | 1.36 | 199.58 | 424.11 | 146.75 | 311.85 |
| P-36 | 29 | 488.92 | 740.14 | 3.34 | 221.75 | 107.54 | 66.39 | 32.20 |
| P-37 | 653.63 | 505.85 | 1253.43 | 75.2 | 229.43 | 182.12 | 3.05 | 2.42 |
| P-38 | 23.84 | 936.7 | 1248.2 | 2.74 | 424.84 | 181.36 | 155.05 | 66.19 |
| P-39 | 196.15 | 716.41 | 638.41 | 22.6 | 324.93 | 92.76 | 14.38 | 4.10 |
| P-40 | 29.94 | 181.65 | | 3.44 | 82.39 | | 23.95 | |
| P-41 | 49.19 | 58.3 | | 5.66 | 26.44 | | 4.67 | |
| P-42 | 19.03 | 154.38 | | 2.19 | 70.02 | | 31.97 | |
| P-43 | 39.51 | 92.52 | | 4.55 | 41.96 | | 9.22 | |
| P-44 | 21.46 | 114.5 | | 2.47 | 51.93 | | 21.02 | |
| P-45 | 40.09 | 157.68 | | 4.61 | 71.52 | | 15.51 | |
| P-46 | 0.83 | 12.11 | 1609.82 | 0.095 | 5.5 | 233.91 | 58 | 2462.2 |
| P-47 | 5.34 | 70.62 | 1808.28 | 0.61 | 32.03 | 262.74 | 52.5 | 430.7 |

[a]rat nNOS;
[b]murine iNOS;
[c]bovine eNOS;
*Indicates no inhibition was observed up to the concentration listed;
**where n/i is Ki(iNOS)/Ki(nNOS) and n/e is Ki(eNOS)/Ki(nNOS).

We claim:

1. A neuronal nitric oxide synthase inhibitor compound of a formula

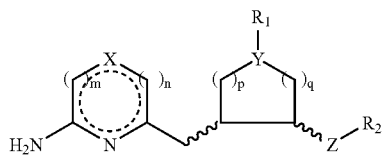

wherein X is CH; m and n are 1; Y is N; p and q are 1; Z is selected from NH and O; R$_1$ is selected from H, alkyl, amino, hydroxyl, and substituted alkyl moieties, said R$_1$ substituents selected from amino, hydroxy and phenyl substituents; and R$_2$ is selected from H, alkyl, substituted alkyl, hydroxyalkyl, substituted hydroxyalkyl, aminoalkyl and substituted aminoalkyl moieties, said R$_2$ substituents selected from alkoxycarbonyl, alkylamido, carbamoyl, pyridinyl, phenylalkyl and phenyl substituents; and a salt thereof.

2. The compound of claim 1 wherein Z is NH, or O, and R$_2$ is an aminoalkyl moiety.

3. The compound of claim 2 wherein said R$_2$ moiety is selected from primary, secondary, and tertiary amino groups.

4. The compound of claim 3 wherein R$_1$ is selected from H and aminoalkyl moieties.

5. The compound of claim 1 wherein Z is NH or O, R$_1$ is selected from H and aminoalkyl moieties, and R$_2$ is an aminoalkyl moiety.

6. A neuronal nitric oxide synthase inhibitor compound of a formula

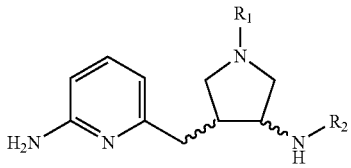

wherein R$_1$ is selected from H, alkyl, substituted alkyl, aminoalkyl, substituted aminoalkyl, hydroxyalkyl, and substituted hydroxyalkyl moieties, said R$_1$ substituents selected from amino, hydroxy and phenyl substituents; and $R_2$ is selected from H, alkyl, substituted alkyl, hydroxyalkyl, substituted hydroxyalkyl, aminoalkyl and substituted aminoalkyl moieties, said $R_2$ substituents selected from alkoxycarbonyl, alkylamido, carbamoyl, pyridinyl and phenyl substituents; and a salt thereof.

7. The compound of claim 6 wherein $R_1$ is selected from H and aminoalkyl moieties.

8. The compound of claim 6 wherein $R_2$ is an aminoalkyl moiety.

9. The compound of claim 8 wherein said $R_2$ moiety is selected from primary, secondary, and tertiary amino groups.

10. The compound of claim 9 wherein $R_1$ is selected from H and aminoalkyl moieties.

* * * * *